United States Patent [19]

Matsuura et al.

[11] Patent Number: 5,472,883
[45] Date of Patent: Dec. 5, 1995

[54] SOLID PHASE REAGENT AND ASSAY METHOD FOR MEASURING ANTIBODIES SPECIFIC TO ANTIPHOSPHOLIPID SYNDROME

[75] Inventors: Eiji Matsuura; Yoshiko Igarashi; Hisato Nagae, all of Choshi; Takao Koike, Minami-go-jo Maruyama City House 401, 1-1, Minami-go-jo Nishi 22-chome, Chuo-ku, Sapporo-shi, Hokkaido 064, all of Japan

[73] Assignees: Yamasa Corporation, Chiba; Takao Koike, Hokkaido, both of Japan

[21] Appl. No.: 133,082

[22] PCT Filed: Feb. 5, 1993

[86] PCT No.: PCT/JP93/00144

§ 371 Date: Oct. 5, 1993

§ 102(e) Date: Oct. 5, 1993

[87] PCT Pub. No.: WO93/16387

PCT Pub. Date: Aug. 19, 1993

[30] Foreign Application Priority Data

Feb. 5, 1992 [JP] Japan .................................. 4-054329
Aug. 12, 1992 [JP] Japan .................................. 4-236517

[51] Int. Cl.⁶ .......................... G01N 33/543; G01N 33/53
[52] U.S. Cl. ............................ 436/518; 422/57; 435/7.1; 435/7.92; 435/7.94; 435/7.95; 435/970; 435/975; 436/528; 436/531; 436/532; 436/808; 530/359; 530/380; 530/389.3
[58] Field of Search ........................ 427/2, 2.13; 422/57; 435/7.1, 7.92–7.95, 177, 180, 970, 975; 436/518, 528, 531, 532, 71, 808, 810; 530/389.3, 380, 359

[56] References Cited

U.S. PATENT DOCUMENTS

| | | | |
|---|---|---|---|
| 4,299,916 | 11/1981 | Litman et al. | 435/6 |
| 4,552,633 | 11/1985 | Kumakura et al. | 204/159.21 |
| 5,016,644 | 5/1991 | Guirguis | 128/771 |
| 5,028,657 | 7/1991 | Hsu et al. | 525/54.1 |
| 5,102,798 | 4/1992 | Guiseppi-Elie | 435/177 |
| 5,133,363 | 7/1992 | Guirguis | 128/771 |
| 5,171,779 | 12/1992 | Hsu et al. | 525/54.1 |
| 5,268,287 | 12/1993 | Matsuki et al. | 435/181 |

FOREIGN PATENT DOCUMENTS

| | | |
|---|---|---|
| 2015938 | 11/1990 | Canada . |
| 0155252 | 9/1985 | European Pat. Off. . |
| 0324603 | 7/1989 | European Pat. Off. . |
| 59-15861 | 1/1984 | Japan . |
| 59-58004 | 4/1984 | Japan . |
| 60-91983 | 5/1985 | Japan . |
| 60-222774 | 11/1985 | Japan . |
| 62-123359 | 6/1987 | Japan . |
| 60-260857 | 6/1987 | Japan . |
| 63-18268 | 1/1988 | Japan . |
| 1-223352 | 9/1989 | Japan . |
| 2-71152 | 3/1990 | Japan . |
| 2-131500 | 5/1990 | Japan . |
| 2-304364 | 12/1990 | Japan . |
| 2-504550 | 12/1990 | Japan . |
| 3-72261 | 3/1991 | Japan . |
| 3-128461 | 5/1991 | Japan . |
| 2148905 | 6/1985 | United Kingdom . |
| 89/1155 | 2/1989 | WIPO . |
| 9115772 | 10/1991 | WIPO . |

OTHER PUBLICATIONS

Chemical Abstract of JP-63-18268, vol. 109: 226254s (1988) p. 433.
Galli et al., "Anticardiolipin Antibodies (ACA) Directed Not to Cardiolipin But To A Plasma Protein Cofactor", Lancet 1990; 335: pp. 1544–1547.
American Journal of Medicine, "Association of Anti–$\beta_2$ Glycoprotein I Antibodies With Lupus–Type Circulating Anticoagulant and Thrombosis in Systemic Lupus Erythematosus", Viard et al., vol. 93, No. 2, 1992 pp. 181–186.
E. Matsura et al., "Anticardiolipin Antibodies Recognize $\beta_2$–Glycoprotein I Structure Altered by Interacting with an Oxygen Modified Solid Phase Surface" in J. Exp. Medicine, vol. 179, Feb. 1994, pp. 457–462.
J. Arvieux et al. "Measurement of Anti–Phospholipid Antibodies by ELISA using $\beta_2$–glycoprotein I as an antigen", J. of Immunol. Methods 143 (1991): 223–229.
J. Hunt et al., "Identification of a region of $\beta_2$–glycoprotein I critical for lipid bending and anti–cardiolipin antibody . . .", PNAS, USA 90 (1993): 2141–2145.

*Primary Examiner*—Carol A. Spiegel
*Attorney, Agent, or Firm*—Wenderoth, Lind & Ponack

[57] ABSTRACT

A solid phase reagent is provided which comprises a carrier having a surface onto which functional groups containing a negative charge or a lone pair of electrons and/or free radicals containing a negative charge or a lone pair of electrons have been introduced and having $\beta_2$-glycoprotein I coated on the surface. Using this reagent, antibodies specific to antiphospholipid syndrome can be specifically assayed. Moreover, antibodies specific to antiphospholipid syndrome can be assayed differentially from antibodies specific to infectious diseases by using the solid phase reagent described above or a further modified solid phase reagent.

15 Claims, 15 Drawing Sheets

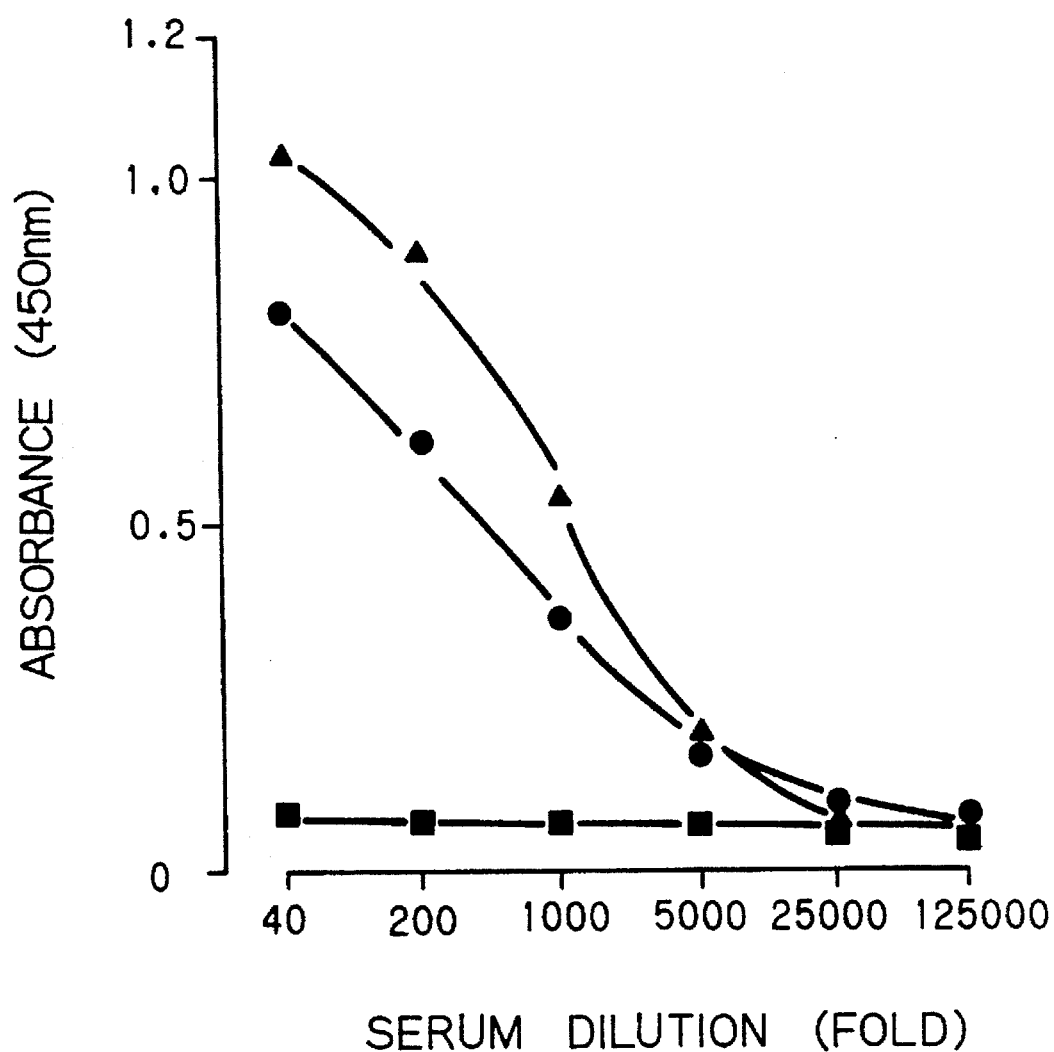
FIG. I
(PRIOR ART)

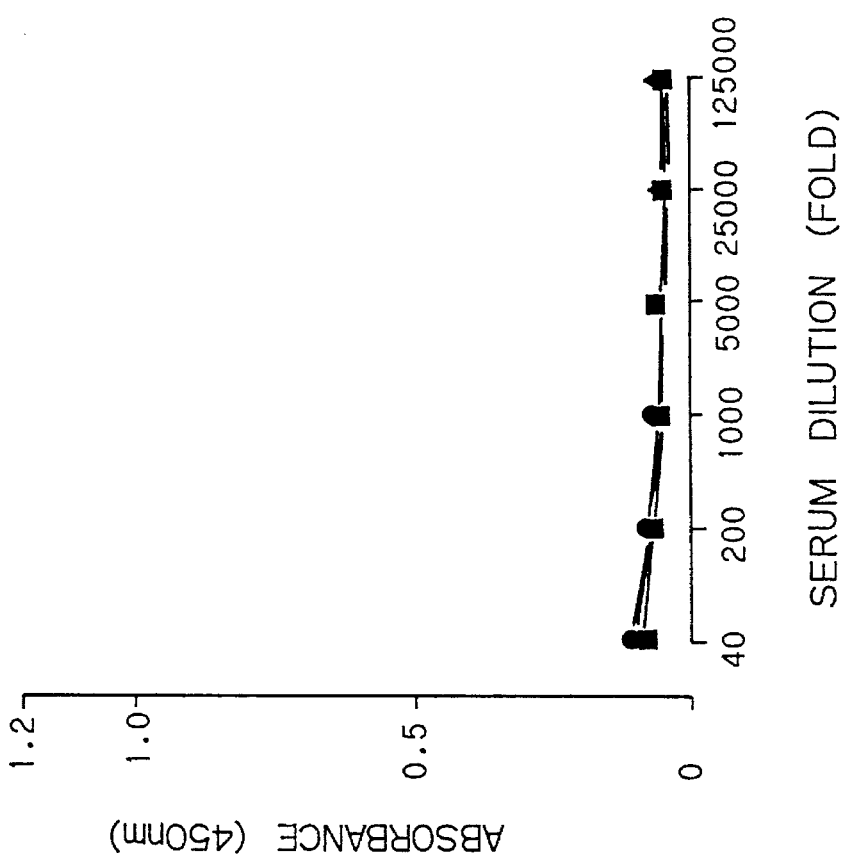
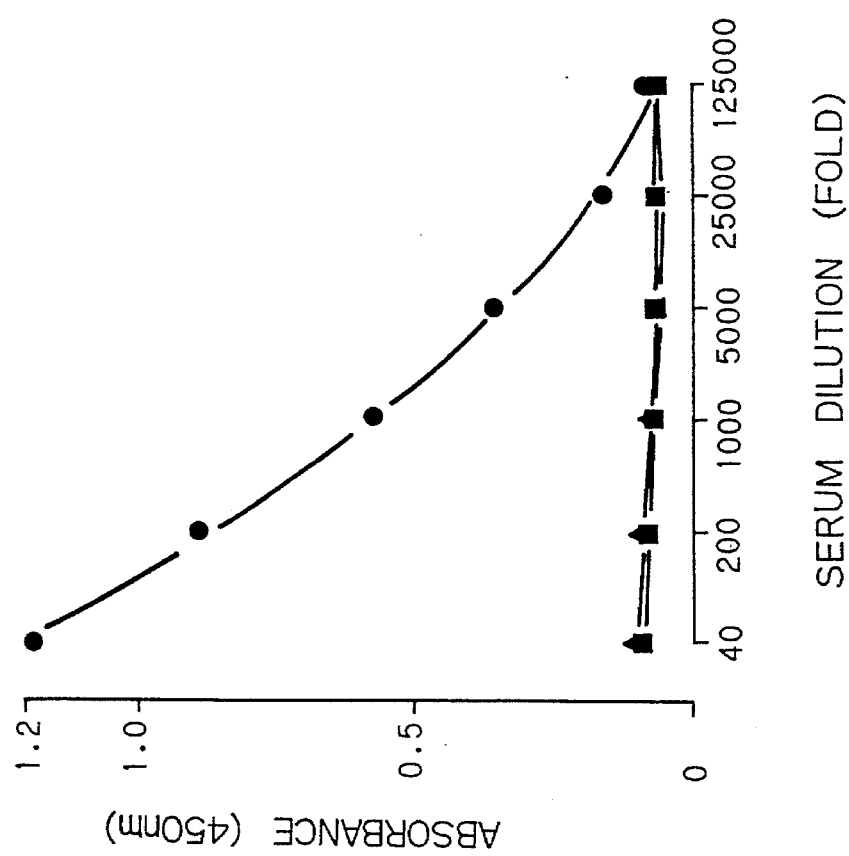
FIG. 3(A)
FIG. 3(B)

FIG. II

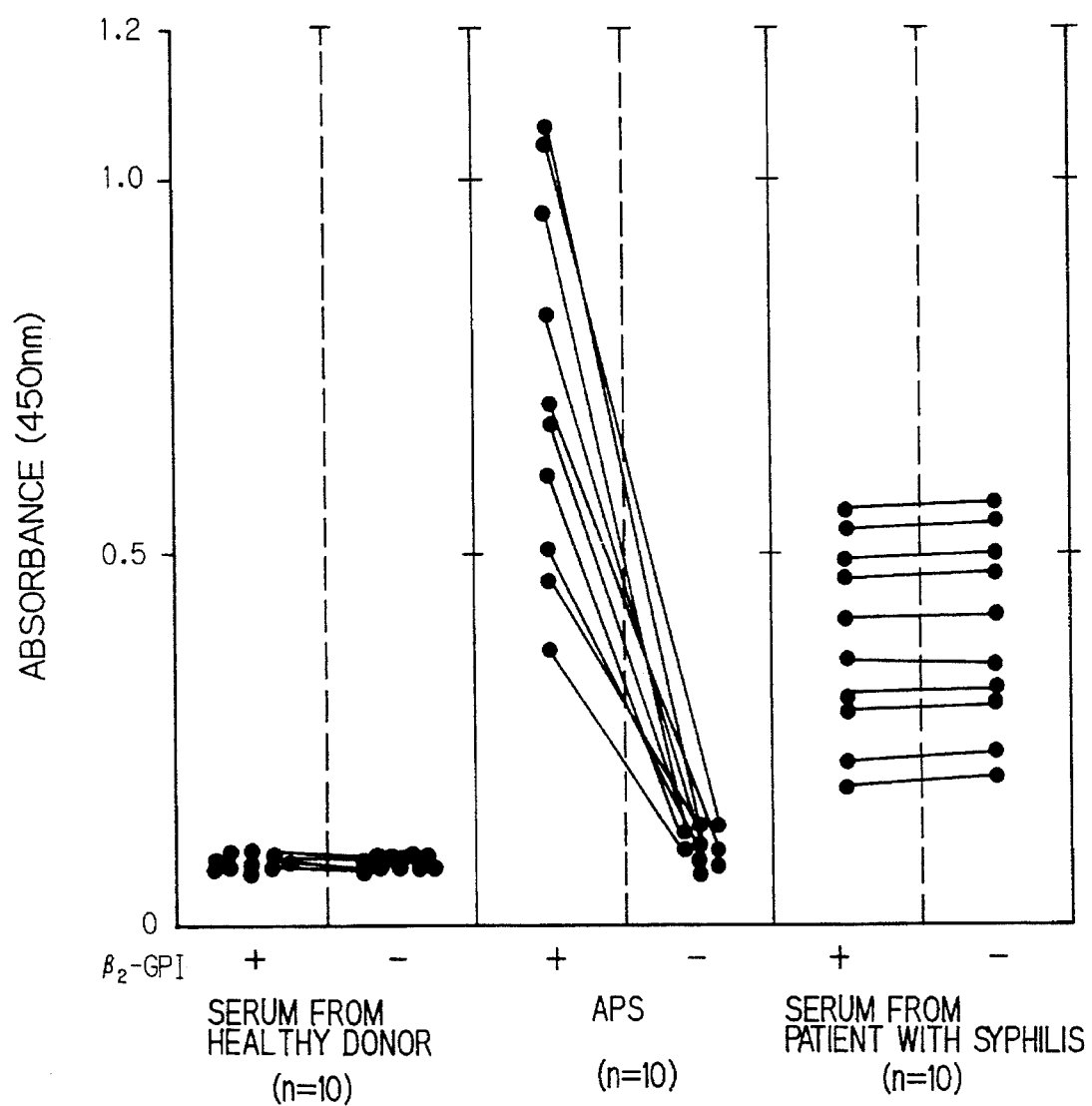

SOLID PHASE REAGENT AND ASSAY METHOD FOR MEASURING ANTIBODIES SPECIFIC TO ANTIPHOSPHOLIPID SYNDROME

BACKGROUND OF THE INVENTION

1. Field of the Invention

The present invention relates to a solid phase reagent obtained by binding β2-glycoprotein I (β2-GPI) to a specific carrier, an assay method for antibodies specific to antiphospholipid syndrome using the solid phase reagent, a method for detecting antibodies specific to antiphospholipid syndrome and antibodies specific to infectious diseases differentially from each other, and a kit for use in the method.

2. Description of Related Art

Various assay methods including RIA and ELISA for anticardiolipin antibodies which are antibodies of the antiphospholipid family had been reported by Harris et al. (Lancet, iii: 1211, 1983), by Koike et al. (Clin. Exp. Immunol., 56: 193, 1984), etc.

However, those methods described above are not necessarily satisfactory since they involve problems in that the anticardiolipin antibodies cannot be assayed quantitatively or they involve problems in that the antibodies associated with infectious diseases cannot be assayed differentially from antibodies found in patients with antiphospholipid syndrome.

Recently, Matsuura et al. found that anticardiolipin antibodies associated with antiphospholipid syndrome do not recognize an immobilized cardiolipin (CL) but the complex of cardiolipin and μ2-glycoprotein I (alternatively termed apolipoprotein H or anticardiolipin cofactor). Further, they developed an assay method for antiphospholipid antibody determination based on the new findings described above, which can overcome the prior art problems as described above (Lancet, 336: 177, 1990, RINSHO MEN-EKI (Clinical Immunology), 22 (Suppl. 15): 170, 1990, WO 91/06006, J. Immunol., 148:3855, 1992).

The studies by Matsuura et al. revealed that anticardiolipin antibodies associated with antiphospholipid syndrome recognize the complex of cardiolipin and β2-glycoprotein I. However, clinical significance of the antibodies has been still unclear. Under these circumstances, clarifying the clinical significance of anticardiolipin antibody binding should elucidate the pathogenesis of antiphospholipid syndrome. This is an important issue to be focused on in the future.

To solve the above-mentioned problems, it is important to develop a more convenient assay method having a high specificity and quantitative property. However, according to the conventional RIA and ELISA methods, it was impossible to detect differentially the antibodies directed to the complex of cardiolipin and β2-glycoprotein I which is found in the patient with antiphospholipid syndrome from those directed to cardiolipin associated with infectious diseases such as syphilis, as described above. Although, the assay method improved by Matsuura et al. could provide differential detection of those antibodies, the preparation of solid phase reagents was still complicated on the other hand. It has thus been desired to establish a more convenient assay method.

Accordingly, an object of the present invention is to provide an assay method in a simpler manner for antibodies specific to the complex of cardiolipin and β2-glycoprotein I.

SUMMARY OF THE INVENTION

As a result of extensive studies to achieve the object described above, the present inventors have found that antibodies specific to antiphospholipid syndrome can be detected by using as a solid phase reagent a β2-glycoprotein I-coated carrier whose surface bears functional groups containing a negative charge or a lone pair of electrons, and/or free radicals containing a negative charge or a lone pair of electrons. The present invention has thus been accomplished.

Accordingly, the present invention relates to a solid phase reagent comprising a β2-glycoprotein I-coated carrier whose surface bears functional groups containing a negative charge or a lone pair of electrons, and/or free radicals containing a negative charge or a lone pair of electrons (hereinafter sometimes simply referred to as solid phase reagent I).

The present invention also relates to an assay method by using the solid phase reagent I for antibodies specific to antiphospholipid syndrome and a kit for use in the method.

The present invention further relates to an assay method for differentially detecting antibodies specific to antiphospholipid syndrome from those specific to infectious diseases and a kit for use in the method.

The present invention further relates to a solid phase reagent for use in the aforesaid differential assay method, which reagent comprises a carrier having a surface onto which functional groups containing a negative charge or a lone pair of electrons, and/or free radicals containing a negative charge or a lone pair of electrons, have been previously introduced and having two sites, one being a site on which β2-glycoprotein I has been coated and the another being a site on which no β2-glycoprotein I has been coated (hereinafter sometimes simply referred to as solid phase reagent II).

BRIEF DESCRIPTION OF THE DRAWINGS

FIG. 1 shows the results obtained by conventional ELISA.

FIGS. 3(A) and 3(B) show the results obtained by the method of the present invention.

FIG. 7 shows the specificity of serum As.

FIG. 14 shows the results of differential assay for anticardiolipin antibodies associated with autoimmune and infectious disease.

DETAILED DESCRIPTION OF THE PREFERRED EMBODIMENTS

Figure 2A:
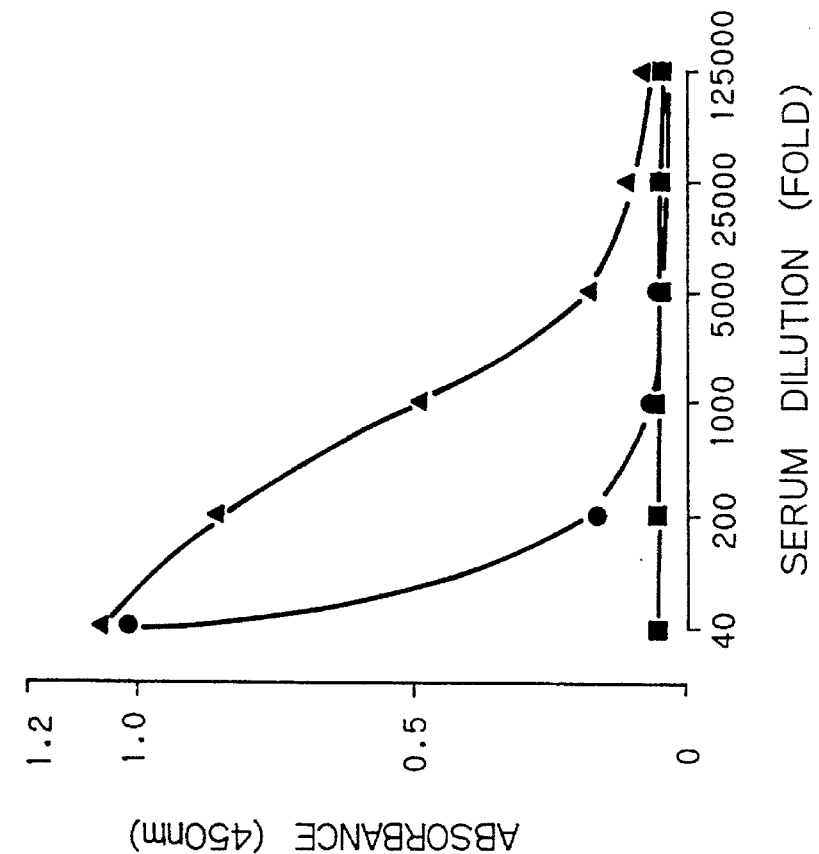
FIGS. 2(A) and 2(B) show the results obtained by the improved method by Matsuura et al.

Hereinafter the present invention is described in more detail.

(1) Solid phase reagent of the present invention

The solid phase reagent I of the present invention comprises a β2-glycoprotein I-coated carrier whose surface bears functional groups containing a negative charge or a lone pair of electrons, and/or free radicals containing a negative charge or a lone pair of electrons.

The solid phase reagent I can be used in the assay method for antibodies specific to an antiphospholipid syndrome and used in the kit therefor.

In the present specification, the term "antiphospholipid syndrome" is used to mean autoimmune diseases including as a representative, example systemic lupus erythematodes (SLE), or a group of diseases showing symptoms such as thrombosis, neuropathy, recurrent abortion, thrombothytopenia, etc. (J. Rheumatol., 13, 486 (1986)).

As the carrier used to coat β2-glycoprotein I thereto, any type of carrier can be used without any particular restriction so long as the carrier has a surface onto which functional groups containing a negative charge or a lone pair of electrons, and/or free radicals containing a negative charge or a lone pair of electrons, have been previously introduced.

Herein, the functional group containing a negative charge or a lone pair of electrons, and/or free radical containing a negative charge or a lone pair of electrons, refers to those containing a negative charge or a lone pair of electrons in the molecule thereof. Specific examples include functional groups such as hydroxy, carboxyl, carbonyl, formyl, imino, nitro, thiol, sulfonyl, etc., and free radicals such as oxygen radicals, etc. Preferred are the functional groups or radicals in which the negative charge or lone pair of electrons is associated with an oxygen atom, for example, hydroxy, carboxyl, carbonyl, oxygen radicals, etc. The carrier having a surface which bears these functional groups and/or free radicals can be prepared by introducing the functional groups containing a negative charge or a lone pair of electrons, directly or if necessary chemically, into a synthetic resin having a highly protein-adsorbable hydrophobic surface, more specifically, a synthetic resin such as polyvinyl chloride, polystyrene, styrene-divinylbenzene copolymer, styrene-maleic anhydride copolymer, nylon, polyacrylamide, polyacrylonitrile, polypropylene, polymethylene methacrylate, etc.

For preparing carriers preferably used in the present invention, the following methods can also be used: a method which comprises exposing the aforesaid synthetic resins having a hydrophobic surface to UV ray, radiations (x ray, β ray, γ ray, etc.), electron beams, or the like to introduce the functional groups containing a negative charge or a lone pair of electrons, and/or free radicals containing a negative charge or a lone pair of electrons onto the hydrophobic surface; a method which comprises treating the aforesaid synthetic resins having a hydrophobic surface with ozone, plasma, etc. to introduce the functional groups containing a negative charge or a lone pair of electrons, and/or free radicals containing a negative charge or a lone pair of electrons, onto the hydrophobic surface; etc.

Such various treatments can be carried out in a conventional manner. For example, in the case that radiation or electron beams are used, the synthetic resins described above are irradiated with approximately 1 to 200 kGray radiation to introduce the functional groups containing a negative charge or a lone pair of electrons and/or free radicals containing a negative charge or a lone pair of electrons onto the hydrophobic surface of the carrier.

Specific examples of such a carrier include EB Plate (manufactured by Labsystems Co., Ltd.), H Type Plate and C Type Plate (manufactured by Sumitomo Bakelite Co., Ltd.), Maxi-Soap Plate (manufactured by Nunc Co., Ltd.), etc.

The carrier can take any one of various types of shapes, such as plate-like type (microtiter plate, disk, etc.), granular type (beads, etc.), tubular type (test tube, etc.), fibrous type, membrane-like type, fine particulate type (latex particles, etc.) and the like. The carrier having an appropriate shape may be chosen depending upon the assay method.

As β2-glycoprotein I which is coated to the carrier, there is no particular restriction so long as it is derived from animal. Especially, β2-glycoprotein I derived from human origin is preferred. β2Glycoprotein I from which the sugar chain has been removed partially or wholly may also be used in the present invention.

β2-Glycoprotein I can be prepared in a conventional manner, for example, by the method of McNeil (Proc. Natl. Acad. Sci. USA, 87: 4120, 1990). Furthermore, the amino acid and nucleotide sequences of β2-glycoprotein I have been already clarified. Thus, β2-glycoprotein I prepared by a conventional peptide synthesis method or DNA recombinant technique can be also used for the present invention.

It is preferred that β2-glycoprotein I be highly purified but this is not so strictly required, either.

β2-Glycoprotein I may be bound to the carrier described above by appropriately combining and conducting conventional processes under suitable conditions known for immobilization of a protein such as an enzyme (cf., KOTEIKA KOSO (Immobilized Enzyme), 1975, edited by Chihata Ichiro, published by Kodansha, SEIKAKAGU JIKKEN KOZA (Series of Biochemical Experiments) 11; Enzyme immunoassay, 1989, published by Tokyo Kagaku Dojin Publishing Co., etc.). For example, any technique of physical adsorption, ionic bonding, covalent bonding, etc. may be used.

The solid phase reagent II of the present invention contains two (2) sites on a carrier, one of which is coated with β2-glycoprotein I and another which is without β2-glycoprotein I, and the surface of the carrier has functional groups containing a negative charge or a lone pair of electrons, and/or free radicals containing a negative charge or a lone pair of electrons previously introduced thereon. The solid phase reagent II is used to detect antibodies specific to antiphospholipid syndrome differentially from those specific to infectious diseases.

The carrier used for the solid phase reagent II, the β2-glycoprotein I and the preparation of the solid phase reagent using these materials are basically the same as in the case of the solid phase reagent I described above, and may be appropriately modified in order to be more suitable for the differential assay according to the present invention.

(2) Method of the present invention and the kit therefor

In the present invention, the assay method for antibodies specific to antiphospholipid syndrome is characterized by using the solid phase reagent I of the present invention described above. So long as the solid phase reagent I is used in the method, the determination principle, conditions, etc. for assay are not particularly restricted.

As the reaction method, for example, there are known a competitive reaction method and a non-competitive reaction method. In the present invention, any of these methods can be adopted. Further as the detection method, there are known a non-labelling method (nephelometry, etc.) for directly detecting the results of an antigen-antibodies reaction, and a labelling method for detecting the results using any marker. Any of these methods is applicable to the present invention. Furthermore, a heterogeneous method which requires BF separation and a homogeneous method which does not require any BF separation are also known, and any of these methods is applicable to the present invention. That is, any assay method suitable for the purpose of the present invention may be appropriately chosen from these known conventional methods.

Details of these conventional methods are described in, for example, the following articles. (1) "RADIOIMMUNOASSAY, Second Series" edited by Hiroshi Irie, published May 1, 1979 by Kodansha Publishing Co., Ltd.

(2) "KOSO-MENEKI SOKUTEIHO (ENZYMEIMMUNOASSAY) (second edition)" edited by Eiji Ishikawa et al., published Dec. 15, 1982 by Igaku-Shoin Publishing Co., Ltd.

(3) RINSHO-BYORI (Clinical Pathology), extra special issue No. 53 "Immunoassay for clinical inspection —technique and application—", published by RINSHO BYORI KANKOKAI, 1983

(4) "Dictionary of Biotechnology", published Oct. 9, 1986 by CMC Publishing Co., Ltd.

(5) "Methods in ENZYMOLOGY Vol. 70" (Immunochemical techniques (Part A))

(6) "Methods in ENZYMOLOGY Vol. 73" (Immunochemical techniques (Part B))

(7) "Methods in ENZYMOLOGY Vol. 74" (Immunochemical techniques (Part C))

(8) "Methods in ENZYMOLOGY Vol. 84" (Immunochemical techniques (Part D: Selected Immunoassay))

(9) "Methods in ENZYMOLOGY Vol. 92" (Immunochemical techniques (Part E: Monoclonal Antibodies and General Immunoassay Methods))

(Articles (5)–(9) were published by Academic Press)

The assay method in accordance with the present invention is described below more specifically, taking as one example an ELISA assay in which a β2-glycoprotein I-coated microtiter plate having a surface onto which the functional groups containing a negative charge or a lone pair of electrons, and/or free radicals containing a negative charge or a lone pair of electrons have been previously introduced, is used as a solid phase reagent.

Firstly, a sample solution (e.g., blood, serum, etc.) is added to each well of β2-glycoprotein I-coated plates to react β2-glycoprotein I with antibodies in the sample solution. Next, after washing the wells, enzyme-labelled anti-immunoglobulin antibodies (e.g., peroxidase-labelled anti-IgG antibodies, etc.) are reacted with the resulting complex followed by separation of the solid phase from the liquid phase. After a substrate (in the case of peroxidase, e.g., hydrogen peroxide and tetramethylbenzidine, etc.) is added to the solid phase or the liquid phase, the enzyme activity in either phase is determined. Finally, the amount of the antibodies corresponding to the measurement data obtained is calculated based on a calibration curve previously prepared.

The kit of the present invention for use in the assay method for antibodies specific to antiphospholipid syndrome is also characterized in that the solid phase reagent I of the present invention described above is comprised as a constituent reagent. Other constituent reagents may be appropriately chosen and used in combination so as to be more suitable for the assay method practiced.

For example, the kit for practicing the ELISA method described above comprises the following reagents. (1) β2-glycoprotein-coated solid phase reagent; (2) enzyme-labeled anti-immunoglobulin antibodies; (3) substrate solution; and, (4) standard antibodies solution having a known concentration.

Next, a differential assay for antibodies specific to antiphospholipid syndrome from antibodies specific to infectious diseases is performed utilizing the reactivity difference between the reaction of the respective antibodies with the site (reagent) to which β2-glycoprotein I has been bound and the reaction of the respective antibodies with the site (reagent) to which no β2-glycoprotein I has been bound. That is, antibodies specific to antiphospholipid syndrome bind specifically to the β2-glycoprotein I-coated site (reagent), whereas antibodies specific to infectious diseases do not show such a tendency. By detecting the reactivity difference, it can be identified from which type the antibodies to be analyzed in a sample are derived, so that the respective antibodies can be assayed differentially from each other.

Therefore, the differential assay can be performed in the same manner as in the aforesaid assay method for antibodies specific to antiphospholipid syndrome described above, except for using either the solid phase reagent II described above or a combination of two solid phase reagents, i.e., the solid phase reagent I obtained by coating with β2-glycoprotein I the carrier whose surface bears the functional groups containing a negative charge or a lone pair of electrons and/or free radicals containing a negative charge or a lone pair of electrons, and the solid phase reagent on which no β2-glycoprotein I has been coated.

The kit for use in the differential assay for antibodies specific to antiphospholipid syndrome and antibodies specific to infectious diseases is also characterized by using either the solid phase reagent II described above or a combination of two solid phase reagents, i.e., the solid phase reagent I obtained by coating with β2-glycoprotein I the carrier whose surface bears the functional groups containing a negative charge or a lone pair of electrons and/or free radicals containing a negative charge or a lone pair of electrons, and the solid phase reagent on which no β2-glycoprotein I has been coated. Other reagents may be appropriately chosen and used in combination so as to be more suitable for the differential assay method practiced.

It has been for the first time found by the present inventors that by using only β2-glycoprotein I, antibodies specific to antiphospholipid syndrome can be specifically detected. Accordingly, the present invention does not require a combination of β2-glycoprotein I and phospholipid for detecting antibodies specific to antiphospholipid syndrome, so that the reagent for use in the assay can be prepared in an extremely simple manner. Furthermore, the method of the present invention shows a high correlation with the results obtained by the improved assay method by Matsuura et al. and can thus be a more simpler method which is used instead of the improved method by Matsuura et al.

Further, by using the solid phase reagent comprising a carrier having the surface onto which functional groups containing a negative charge or a lone pair of electrons, and/or free radicals containing a negative charge or a lone pair of electrons have been introduced, and having a site on which β2-glycoprotein I has been coated and another site on which no β2-glycoprotein I has been coated; or by using the combination of two solid phase reagents, i.e., the solid phase reagent I comprising a β2-glycoprotein I-coated carrier of which whose surface bears the functional groups containing a negative charge or a lone pair of electrons and/or free radicals containing a negative charge or a lone pair of electrons and the solid phase reagent on which no β2-glycoprotein I has been coated, antibodies specific to antiphospholipid syndrome can be differentially assayed from antibodies specific to infectious diseases.

Hereinafter, the present invention is more specifically described by referring to Comparative Examples and Examples.

Comparative Example 1: Conventional ELISA

An ethanolic solution of 50 μg/ml of bovine heart-derived cardiolipin (manufactured by Sigma) was added to each well of 96-well microtiter plates (polystyrene; manufactured by Labsystems Co., Ltd.) in an amount of 50 μl each/well. Ethanol in the well was evaporated under reduced pressure. After drying, 250 μl of phosphate buffered saline (PBS) containing 10% fetal bovine serum (PBS–FBS) (pH 7.4) was added to the each well. The wells were incubated for an hour at room temperature, and then washed three times with 200 μl of PBS containing 0.05% (V/V) TWEEN 20 (trademark, manufactured by Kishida Chemical Co., Ltd.) (PBS-TWEEN).

Next, 100 μl each of serum sample appropriately diluted with PBS–FBS was added to each well and the reaction was carried out at room temperature for an hour, followed by washing three times with 200 μl each of PBS-TWEEN. Then 100 μl each of horseradish peroxidase-labeled anti-human IgG antibodies was added to each well and the reaction was carried out at room temperature for an hour, followed by washing three times with 200 μl each of PBS-TWEEN. After 100 μl of substrate solution [0.3 mM 3,3',5,5'-tetramethylbenzidine (TMBZ) solution containing 0.003% hydrogen peroxide] was added to react them at room temperature for 10 minutes, 100 μl of a reaction terminator (2N sulfuric acid) was added to the reaction solution. Absorbance at 450 nm was then measured. The enzyme-labeled antibodies used were obtained by conjugating horseradish peroxidase to mouse monoclonal anti-human IgG antibodies (G-O2, IgG class, manufactured by Yamasa Corporation) according to the periodic acid crosslinking method.

The results are shown in FIG. 1, wherein the circle, triangle and square symbols designate serum collected from a patient with typical antiphospholipid syndrome (SLE and recurrent abortion), serum collected from a patient with syphilis and serum collected from a healthy donor, respectively. As is clearly shown in noted FIG. 1, the conventional method fails to quantitatively determine antibodies specific to antiphospholipid syndrome differentially from antibodies specific to infectious diseases.

Comparative Example 2: Improved method by Matsuura et al. (WO 91/06006)

An ethanolic solution of 50 μg/ml of bovine heart-derived cardiolipin (manufactured by Sigma) was added to each well of 96-well microtiter plates (polystyrene; manufactured by Labsystems Co., Ltd.) in an amount of 50 μl each/well. Ethanol in the well was evaporated under reduced pressure. After drying, 200 μl of phosphate buffered saline (PBS) containing 1% purified bovine serum albumin (containing no bovine β2-glycoprotein I) (PBS-pBSA) (pH 7.4) was added to the each well. The wells were incubated for an hour at room temperature, and then washed three times with 250 μl of PBS containing 0.05% (V/V) TWEEN 20 (trademark, manufactured by Kishida Chemical Co., Ltd.) (PBS-TWEEN).

Next, 50 μl each/well of purified human β2-glycoprotein I (prepared into 30 μg/ml with PBS-pBSA) was added to each well (50 μl each/well of PBS-pBSA was added to the control group). After allowing to stand for 10 minutes, 50 μl each of serum sample appropriately diluted with PBS-pBSA was added to each well and the reaction was carried out at room temperature for 30 minutes. After washing three times with 200 μl each of PBS-TWEEN, 100 μl each of horseradish peroxidase-labeled anti-human IgG antibodies was added to each well and the reaction was carried out at room temperature for an hour, followed by washing three times with 200 μl each of PBS-TWEEN. After 100 μl of substrate solution [0.3 mM 3,3',5,5'-tetramethylbenzidine (TMBZ) solution containing 0.003% hydrogen peroxide] was added to react them at room temperature for 10 minutes, 100 μl of a reaction terminator (2N sulfuric acid) was added to the reaction solution. Absorbance at 450 nm was then measured.

Figure 2B:
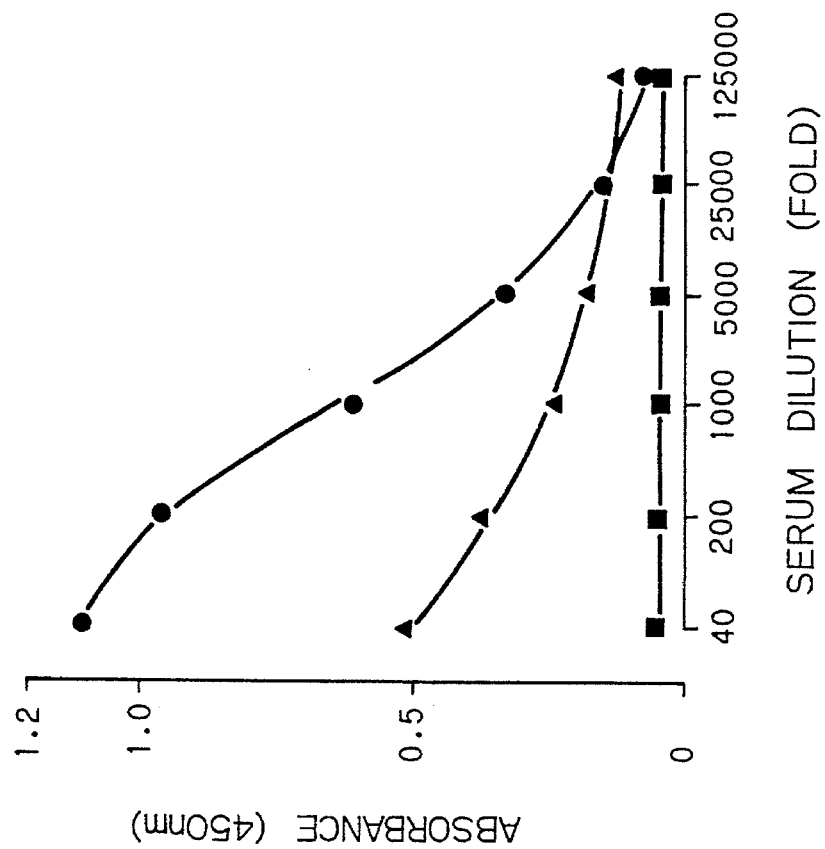

The results are shown in FIG. 2. In FIG. 2, panel (A) and panel (B) designate the group added with β2-glycoprotein I and the group added with none (control group), respectively. The circle, triangle and square symbols have the same significance as in FIG. 1.

By assaying the control group simultaneously, dependency of antibodies in the sample solution on β2-glycoprotein I can be verified, so that antibodies specific to antiphospholipid syndrome can be assayed differentially from antibodies specific to infectious diseases.

Example 1: Assay for antiphospholipid antibodies using solid phase reagent comprising β2-glycoprotein I-coated polystyrene microtiter plates which were previously irradiated with D ray or electron beams:

Purified human β2-glycoprotein I (10 μg/ml:

prepared by 10 mM Hepes (pH 7.4) containing 150 mM NaCl (Hepes)) was added to a polystyrene plate (COMBI PLATE EB (trademark), Labsystems Co., Ltd., Finland) previously irradiated with β ray or electron ray in a volume of 50 μl each/well followed by incubation at 4° C. overnight. After washing three times with 200 μl of PBS-TWEEN, 100 μl each of serum sample appropriately diluted with Hepes-pBSA was added to each well and allowed to stand at room temperature for 30 minutes. After washing with 200 μl of PBS-TWEEN three times, 100 μl each of horseradish peroxidase-labeled anti-human IgG antibodies was added to each well and the reaction was carried out at room temperature for an hour. After washing three times with 200 μl each of PBS-TWEEN, 100 μl of substrate solution [0.3 mM 3,3',5,5'-tetramethylbenzidine (TMBZ) solution containing 0.003% hydrogen peroxide] was added to react them at room temperature for 10 minutes. Then 100 μl of a reaction terminator (2N sulfuric acid) was added to the reaction solution. Absorbance at 450 nm was then measured.

The results are shown in FIG. 3. In FIG. 3, panel (A) and panel (B) designate the results obtained using the polystyrene plate irradiated with β ray or electron beams and the results obtained using a non-irradiated polystyrene plate manufactured by the same company as in the above plate, respectively. The circle, triangle and square symbols have the same significance as in FIG. 1.

As is clearly shown in FIG. 3, the results reveal that antibodies associated with antiphospholipid syndrome can be specifically assayed.

Figure 4:
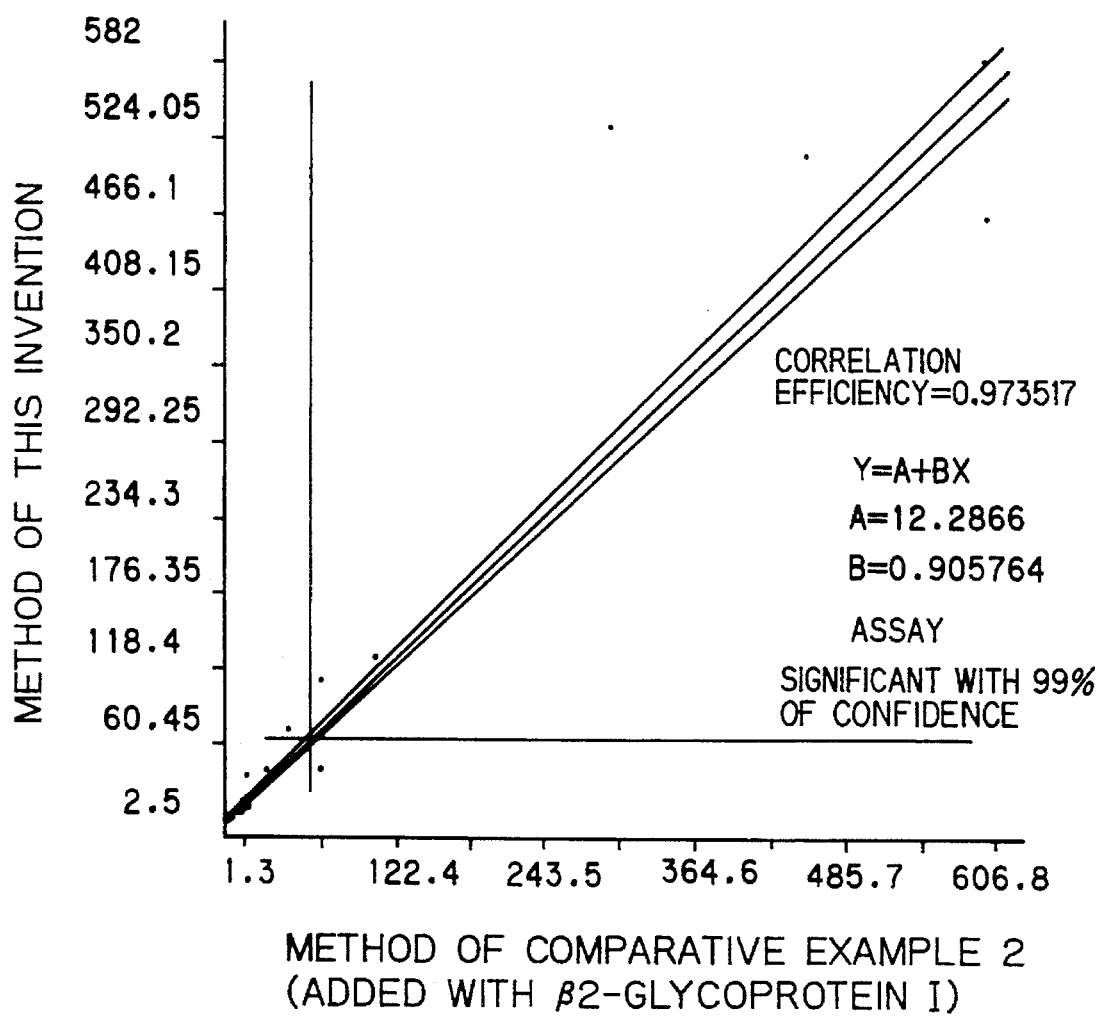
FIG. 4 indicates the correlation between the results obtained by the method of the present invention and those obtained by the improved method of Matsuura et al.

Table 1 described below and FIG. 4 show the correlation between the two results which were obtained by assaying antiphospholipid antibody titers in sera collected from patients with antiphospholipid syndrome (19 cases) and from healthy donors (20 cases) by the two methods, i.e., the method described in Reference Example 2 and the method of the present invention. As a result, there is seen on extremely high correlation (correlation efficiency: 0.97, N=39) between the results obtained in the assay by adding β2-glycoprotein I of Reference Example 2 and the results obtained by the method of the present invention. It has thus been verified that the method of the present invention enables one to assay for antibodies in the sera to the complex of anticardiolipin and β2-glycoprotein I, as in the method of Reference Example 2.

TABLE 1

| | Method of Comparative Example 2 | | |
| --- | --- | --- | --- |
| | β2-Glycoprotein I | | Method of |
| Serum | (+) | (−) | This Invention |
| APS | | | |
| 1 | 16.4 | 3.0 | 20.1 |
| 2 | 37.0 | <1.3 | 69.6 |
| 3 | 19.4 | 3.3 | 5.9 |
| 4 | 62.0 | 2.8 | 22.1 |
| 5 | 6.3 | 2.1 | 9.6 |
| 6 | 5.8 | 1.3 | 9.0 |
| 7 | 4.6 | <1.3 | 11.2 |
| 8 | 460.4 | 8.2 | 509.2 |
| 9 | 5.8 | <1.3 | 23.0 |
| 10 | 8.8 | 2.3 | 6.9 |
| 11 | 2.3 | <1.3 | 5.9 |
| 12 | 44.2 | 1.5 | 58.2 |
| 13 | 64.2 | 3.5 | 18.3 |
| 14 | 604.8 | 10.8 | 582.0 |
| 15 | 3.7 | 2.3 | 35.7 |
| 16 | 53.3 | <1.3 | 188.8 |
| 17 | 19.2 | <1.3 | 40.6 |
| 18 | 606.8 | 10.0 | 463.0 |
| 19 | 108.2 | 3.6 | 125.0 |
| Normal | | | |
| 1 | <1.3 | <1.3 | 4.9 |
| 2 | <1.3 | <1.3 | 3.6 |
| 3 | <1.3 | <1.3 | 3.5 |
| 4 | 2.4 | 1.5 | 6.9 |
| 5 | <1.3 | <1.3 | 5.6 |
| 6 | <1.3 | <1.3 | 5.1 |
| 7 | <1.3 | <1.3 | 5.6 |
| 8 | <1.3 | <1.3 | 4.9 |
| 9 | <1.3 | <1.3 | 4.8 |
| 10 | <1.3 | <1.3 | 2.5 |
| 11 | <1.3 | <1.3 | 5.3 |
| 12 | <1.3 | <1.3 | 4.7 |
| 13 | <1.3 | <1.3 | 5.2 |
| 14 | <1.3 | <1.3 | 4.2 |
| 15 | <1.3 | <1.3 | 4.7 |
| 16 | <1.3 | 1.9 | 4.8 |
| 17 | <1.3 | <1.3 | 5.8 |

TABLE 1-continued

| | Method of Comparative Example 2 | | |
| --- | --- | --- | --- |
| | β2-Glycoprotein I | | Method of |
| Serum | (+) | (−) | This Invention |
| 18 | <1.3 | <1.3 | 3.8 |
| 19 | <1.3 | <1.3 | 3.5 |
| 20 | <1.3 | <1.3 | 4.4 |
| | | | (unit/ml) |

APS: patient with antiphospholipid syndrome
Normal: healthy donor

Example 2 Antibodies used herein WB-CAL-1 and WB-CAL-3:

Monoclonal anticardiolipin antibodies WB-CAL-1 and WB-CAL-3 (both are IgG class) are secreted from hybridomas established by cell fusion of myeloma cells with spleen cells from F1 mouse of NZW mouse and BXSB mouse, respectively. The two antibodies have specificity to the complex of cardiolipin (CL) and β2-glycoprotein I (β2-GPI).

As:

Serum as is a serum collected from an anticardiolipin antibody positive patient with antiphospholipid syndrome. The serum is reactive with the complex of CL and β2-GPI.

Cof-18:

Monoclonal antibody Cof-18 is obtained from purified human β2-GPI-immunized BALB/c mouse. The monoclonal antibody shows reactivity with β2-GPI (PCT/JP92/00528).

(A): Reactivity of anticardiolipin antibodies with β2-GPI-coated plate irradiated with radiation:

To each well of a 96-well micro test plate [MS-3496F (S type, manufactured by Sumitomo Bakelite Co., Ltd.)] which had been previously exposed to radiations having different doses [γ ray (100, 50, 25, 12.5, 6.3, 3.1, 1.6 kGray) and β ray (or electron beam) (50, 25 kGray)] was added 50 μl of purified human β2-GPI (10 μg/ml, prepared with 150 mM NaCl-containing 10 mM Hepes (pH 7.4) (Hepes)). The system was allowed to stand at 4° C. overnight. After washing each well three times with 200 μl of phosphate buffered physiological saline containing 0.05% TWEEN 20 (PBS-TWEEN), 200 μl of 3% gelatin-PBS was added thereto, and then subjected to a blocking treatment by allowing to stand at room temperature for an hour. After gelatin-PBS was removed, 100 μl each of various anticardiolipin antibodies [WP-CAL- 1 (500 ng/ml), WB-CAL-3 (500 ng/ml), serumAs (200-fold dilution)] and monoclonal anti-β2-GPI antibodies (Cof-18, 500 ng/ml) were added to the system, respectively, followed by allowing to stand at room temperature for 30 minutes. After washing three times with PBS-TWEEN, 100 μl each of horseradish peroxidase-labeled anti-mouse IgG antibodies (HRP-amIg) or horseradish peroxidase-labeled anti-human IgG antibodies (HRP-ahIg), each of which had been appropriately diluted, was added to each well and then allowed to stand for 30 minutes. After washing, 100 μl of 0.3 mM tetramethylbenzidine (TMBZ) solution containing 0.003% hydrogen peroxide was added to the mixture. Accurately 10 minutes later, 100 μl of 2N sulfuric acid was added to terminate the reaction. Absorbance was measured at 450 nm.

Figure 5:
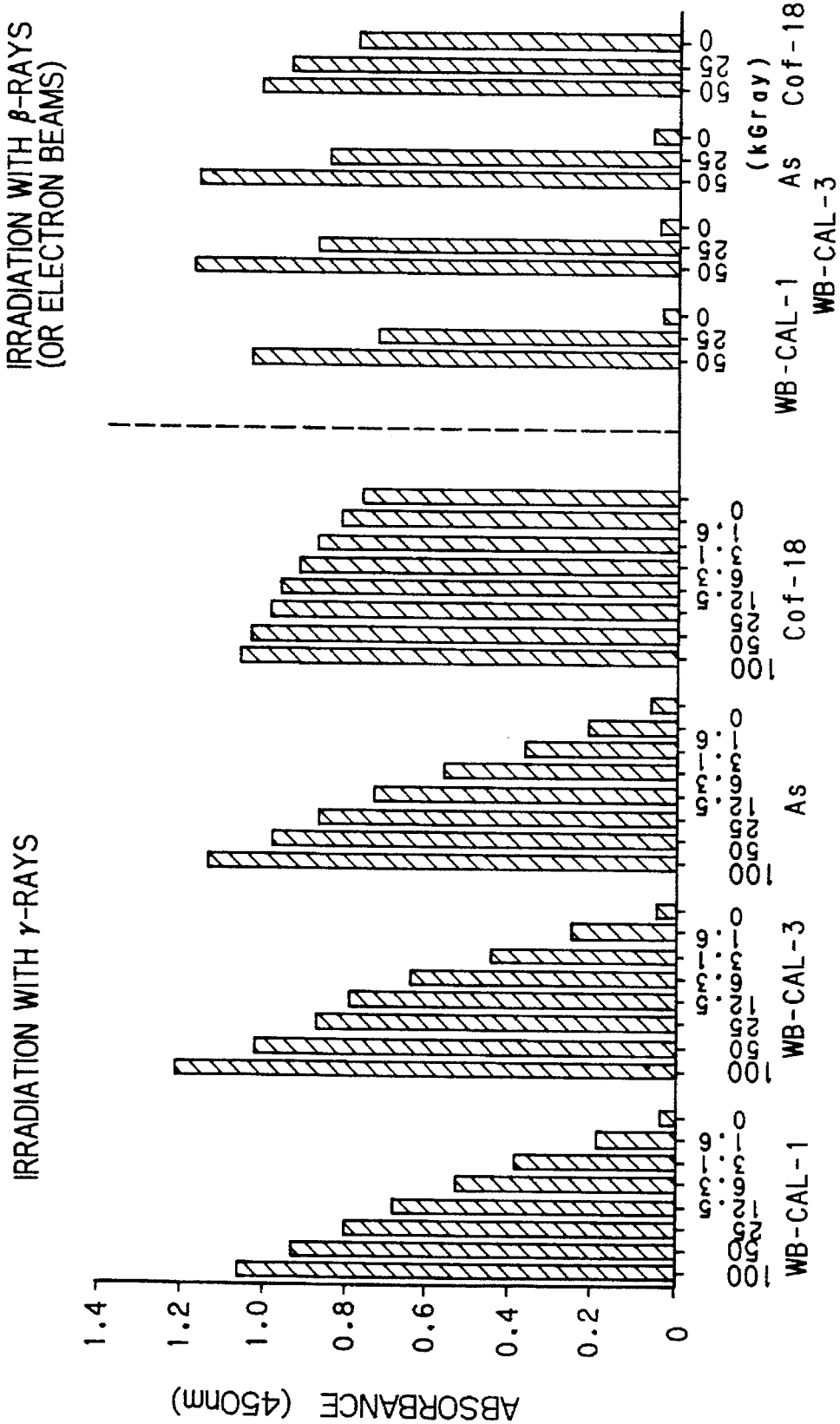
FIG. 5 shows the reactivity of anticardiolipin antibodies with β2-GPI-coated plates which were previously irradiated with radiation or electron beam.

As shown in FIG. 5, all of the three anticardiolipin antibodies showed reactivity dependent on doses of radiations (γ ray, β ray) or electron beams. Such dependency was also noted with Cof-18, but significant binding was observed also in the non-exposure group, indicating that the dependency was different from the reaction specificity of the anticardiolipin antibodies.

(B): Specificity of anticardiolipin antibodies

A β2-GPI coated plate was prepared in a manner similar to the above assay (A). In this inhibition test, four kinds of reagents: CL micelle, β2-GPI solution, CL-coated latex and β2-GPI-bound CL-coated latex were used. The procedures of the preparation are briefly shown below.

CL micelle:

CL micelle was prepared by drying ethanol up from a CL ethanol solution (manufactured by Sigma) into a film shape and then dispersing and suspending the film with a vortex and a bath sonicator.

β2-GPI solution:

The solution was prepared by diluting purified human β2-GPI with Hepes buffer.

CL-coated latex:

After colloidal silica was removed from latex beads (6.4 μm, Seradyn Co., Ltd.), Cl was coated thereto.

β2-GPI-bound CL-coated latex:

The β2-GPI-bound CL-coated latex was prepared by incubating CL latex in a β2-GPI solution and removing free β2-GPI by centrifugation.

Figure 6:
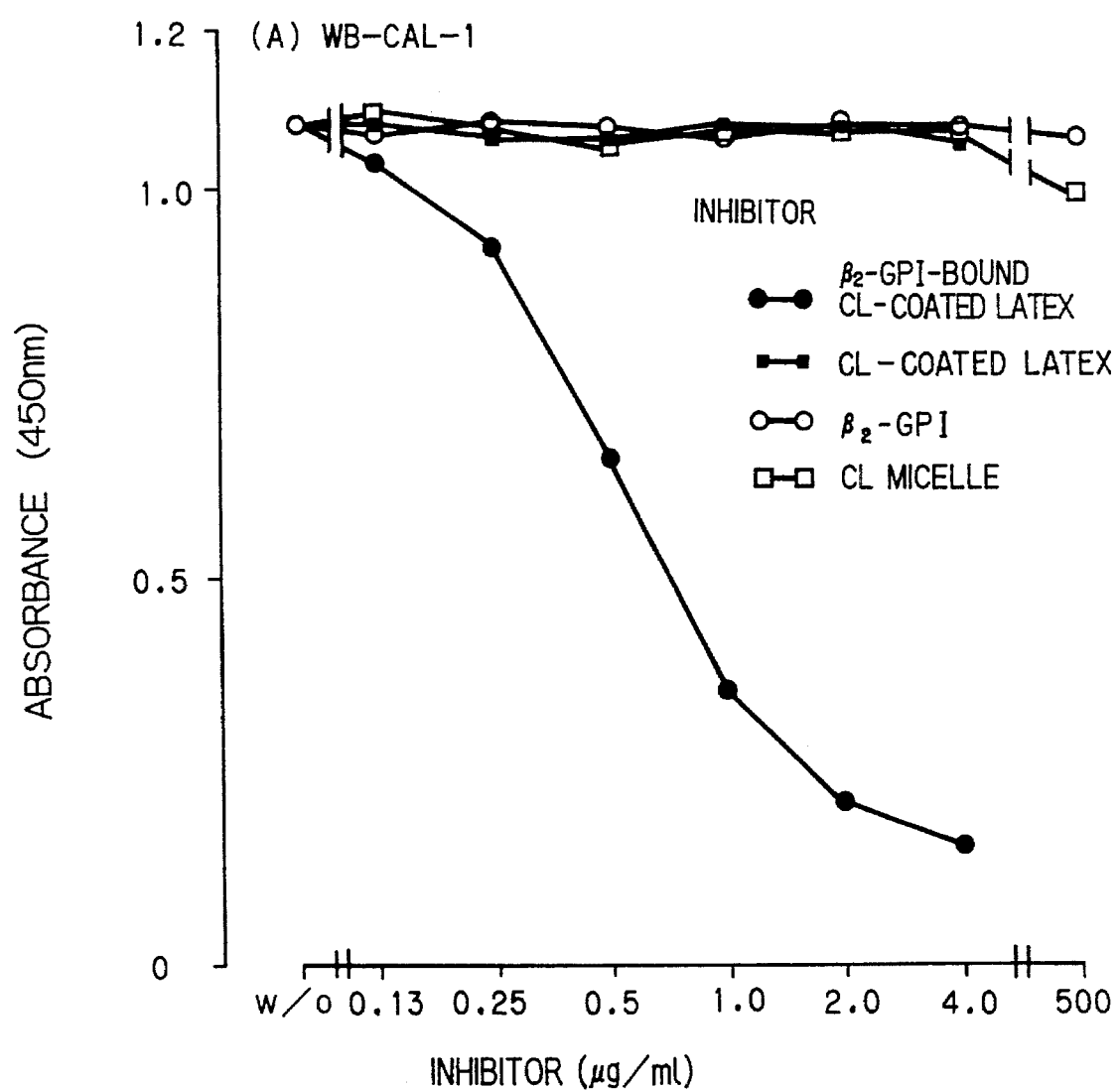
FIG. 6 shows the specificity of monoclonal antibody WB-CAL-1.
Figure 7:
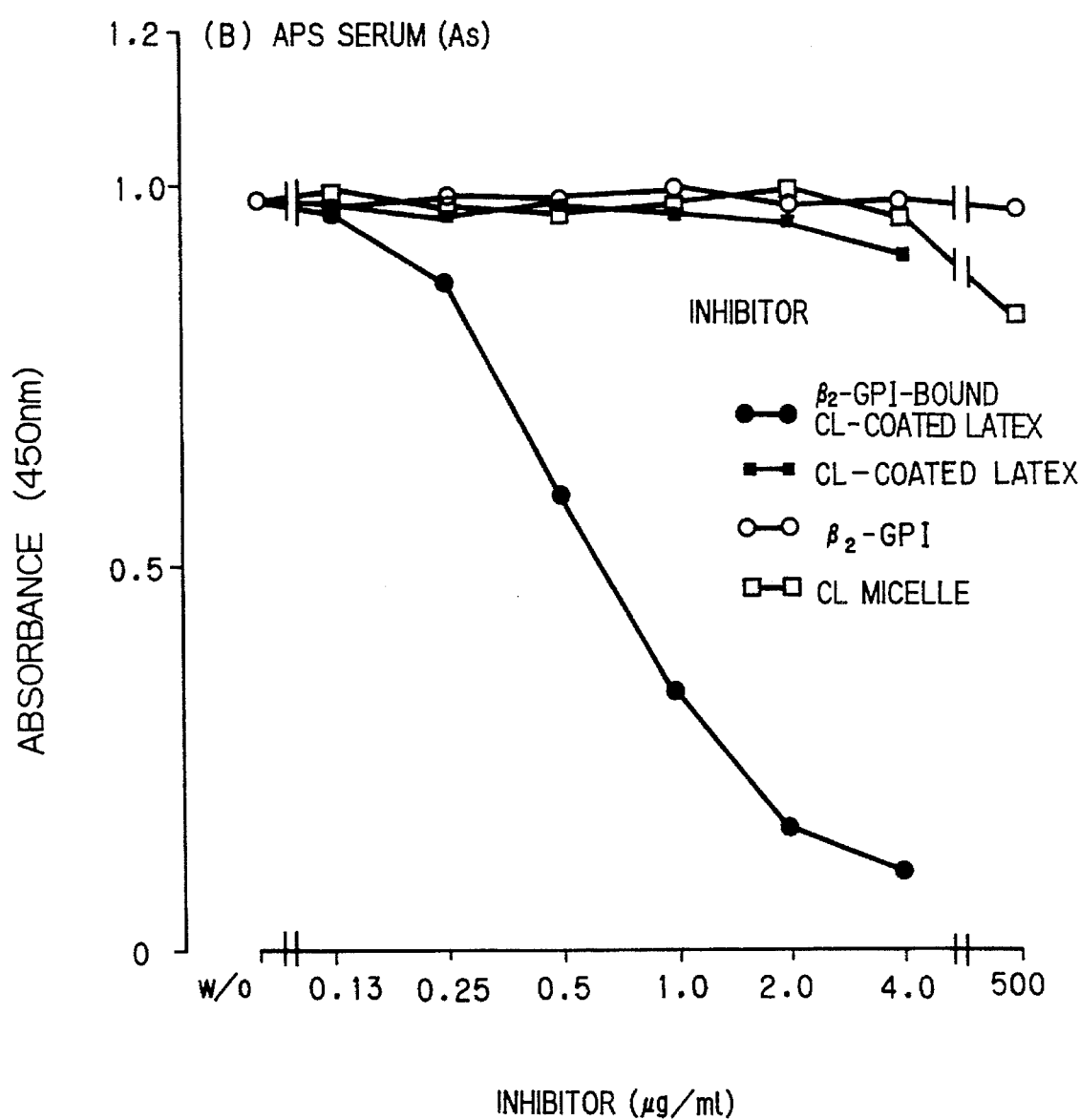
Figure 8:
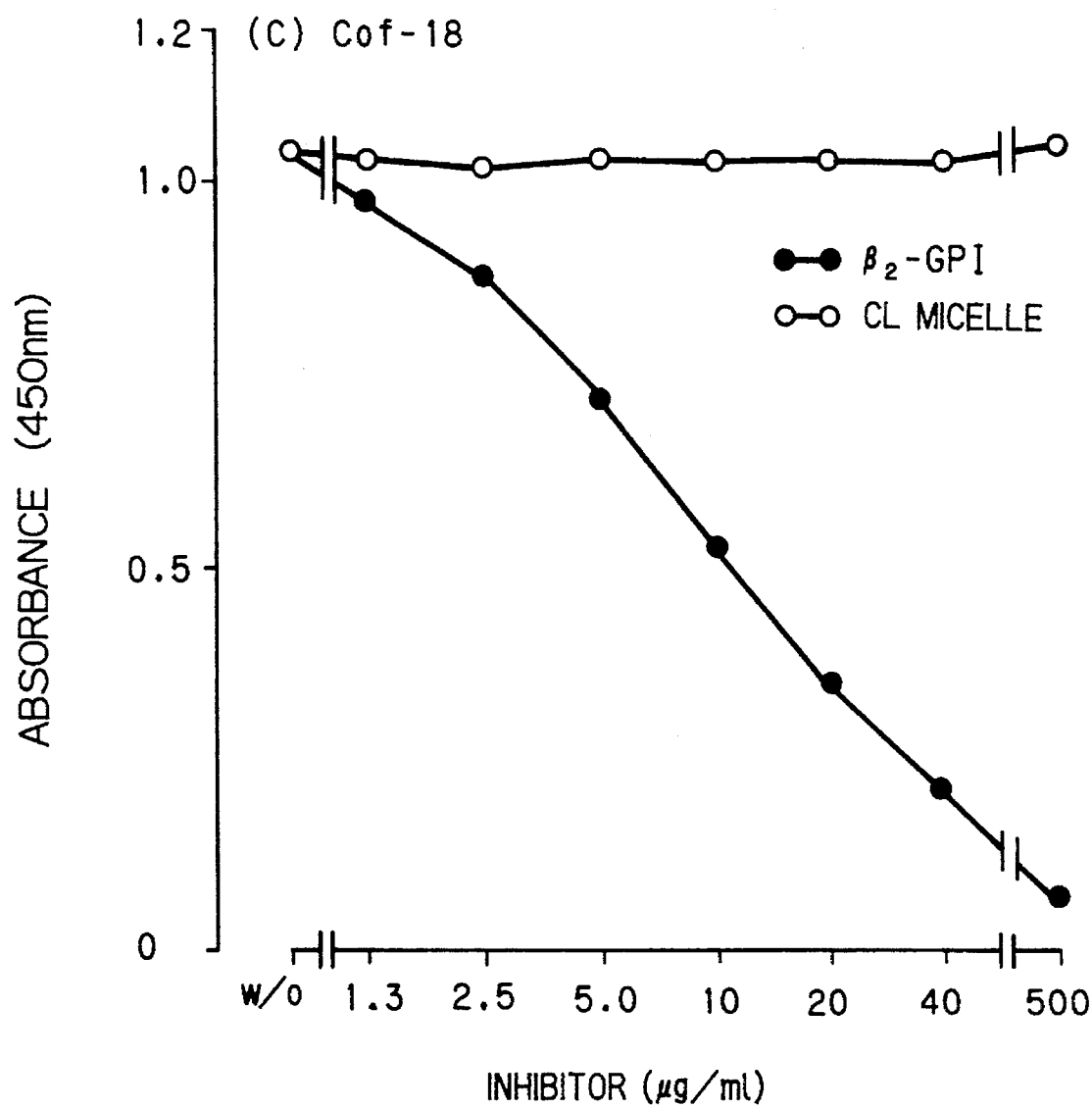
FIG. 8 shows the specificity of anti-β2-GPI antibody (Cof-18).

Monoclonal antibody WB-CAL-1 (500 ng/ml) or serum As (200-fold dilution) was adjusted into the respective concentrations shown in FIG. 6 or FIG. 7, and then added to β2-GPI-coated plate, followed by reacting them at room temperature for 30 minutes. The following procedures for determining the amount of antibodies bound were carried out in the same manner as in the above assay (A). As shown in FIGS. 6 and 7, the binding of anticardiolipin antibodies to the coated β2-GPI occurred only on the β2-GPI-bound CL-coated latex and was inhibited in a dose dependent manner. For information, the results of specificity test of anti-β2-GPI antibodies are shown in FIG. 8. As the result, the binding of anti-β2-GPI antibody (Cof-18) to the coated β2-GPI was inhibited by β2-GPI in a dose dependent manner.

(C): Assay for anticardiolipin antibodies using polystyrene plate onto which carboxyl groups were chemically introduced β2-GPI was coated on a polystyrene plate onto which carboxyl groups had been chemically introduced (carboxylated plate) in a manner similar to the above assay (A) and the amount of anticardiolipin antibodies bound was quantitatively determined by the same procedures as in the above assay (A).

Figure 9A:
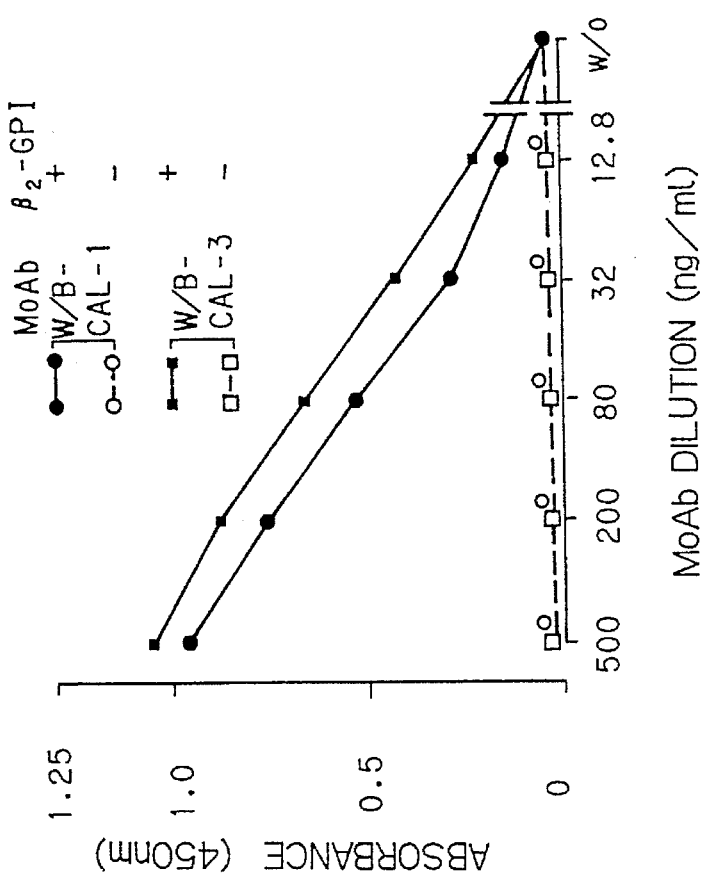
FIG. 9(A) and 9(B) show the results of anticardiolipin determination using carboxylated plates.
Figure 9B:
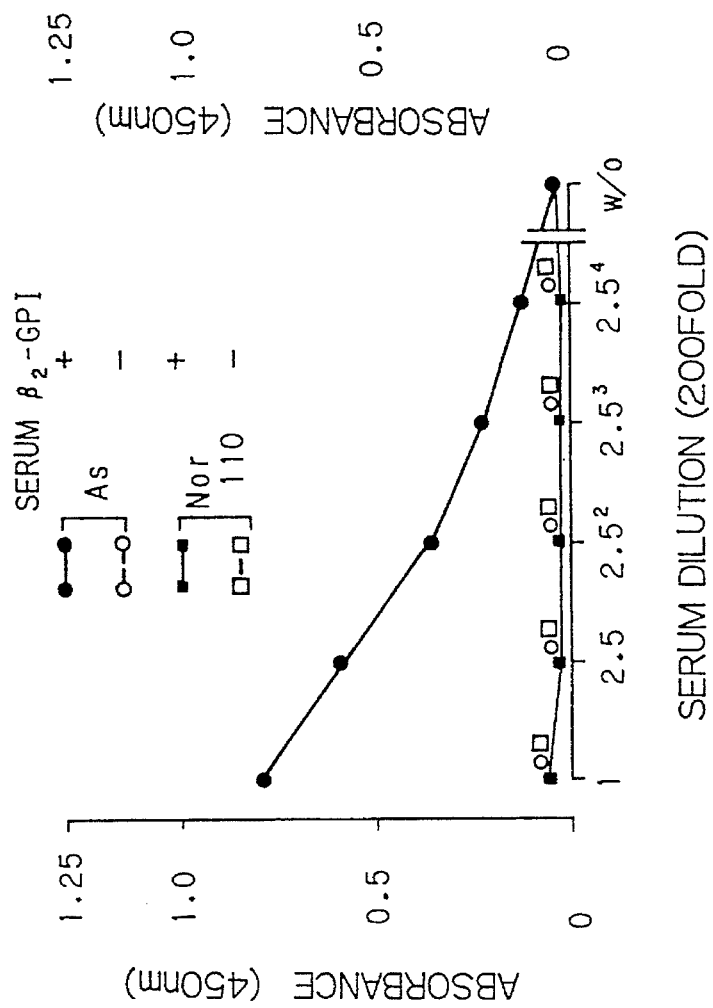

As the a result, monoclonal antibodies WB-CAL-1 and WB-CAL-3 showed specific binding to the β2-GPI coated plates, as shown in FIG. 9. Serum collected from a healthy donor as a control showed no binding under any conditions.

Figure 10:
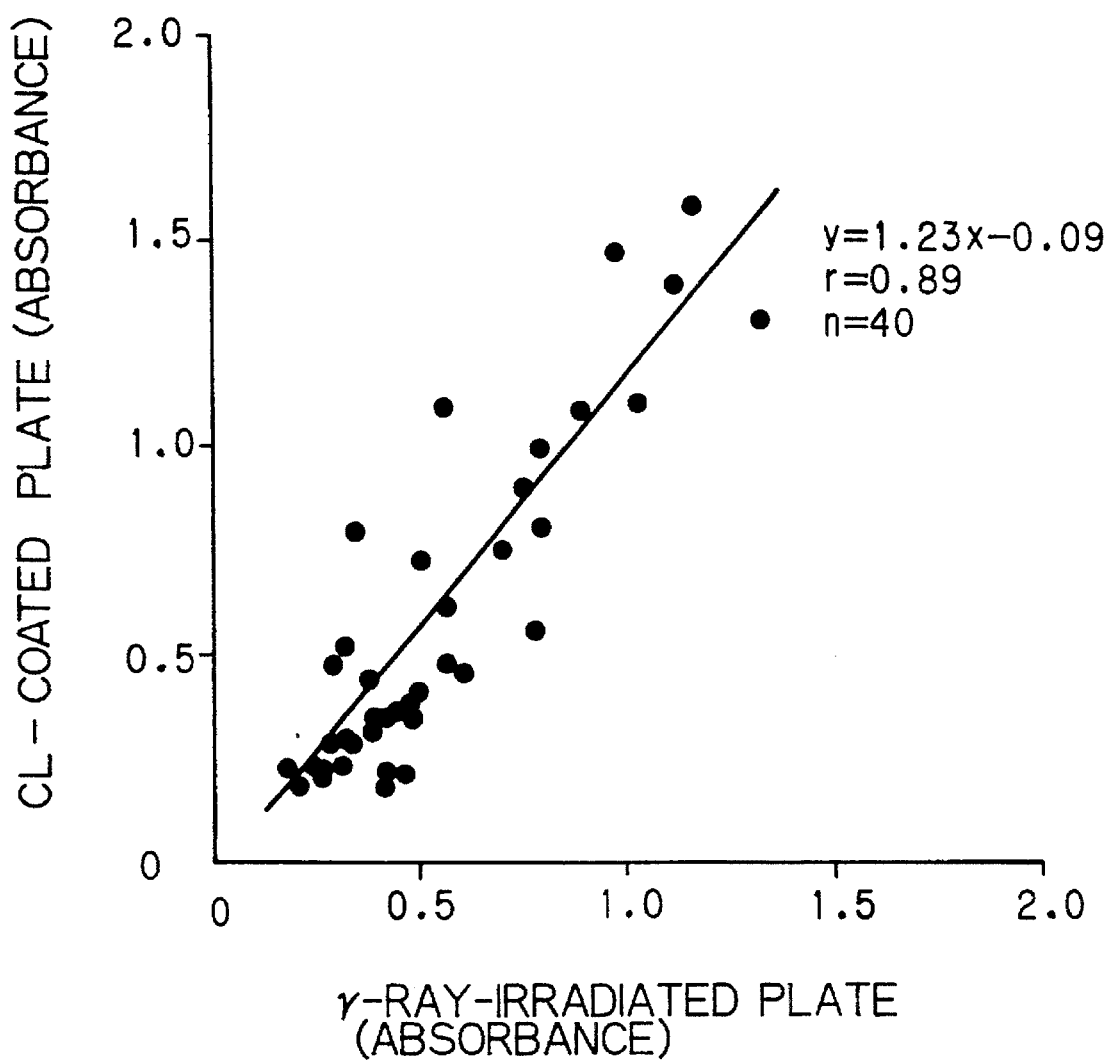
FIG. 10 shows the correlation between anticardiolipin antibody titers obtained using plates irradiated with radiation and those obtained using CL-coated plates.
Figure 11:
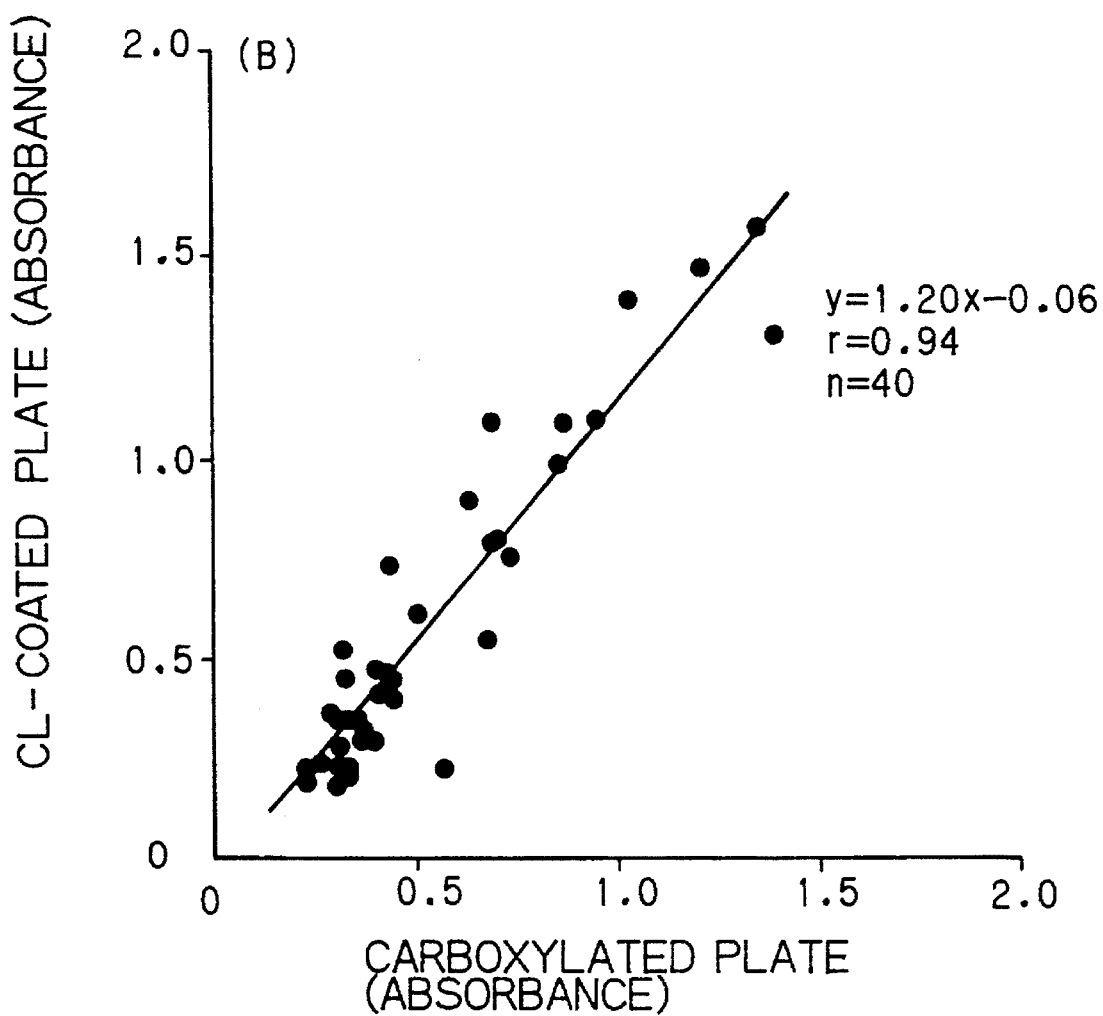
FIG. 11 shows the correlation between anticardiolipin antibody titers obtained using carboxylated plates and those obtained using CL-coated plates.
Figure 12:
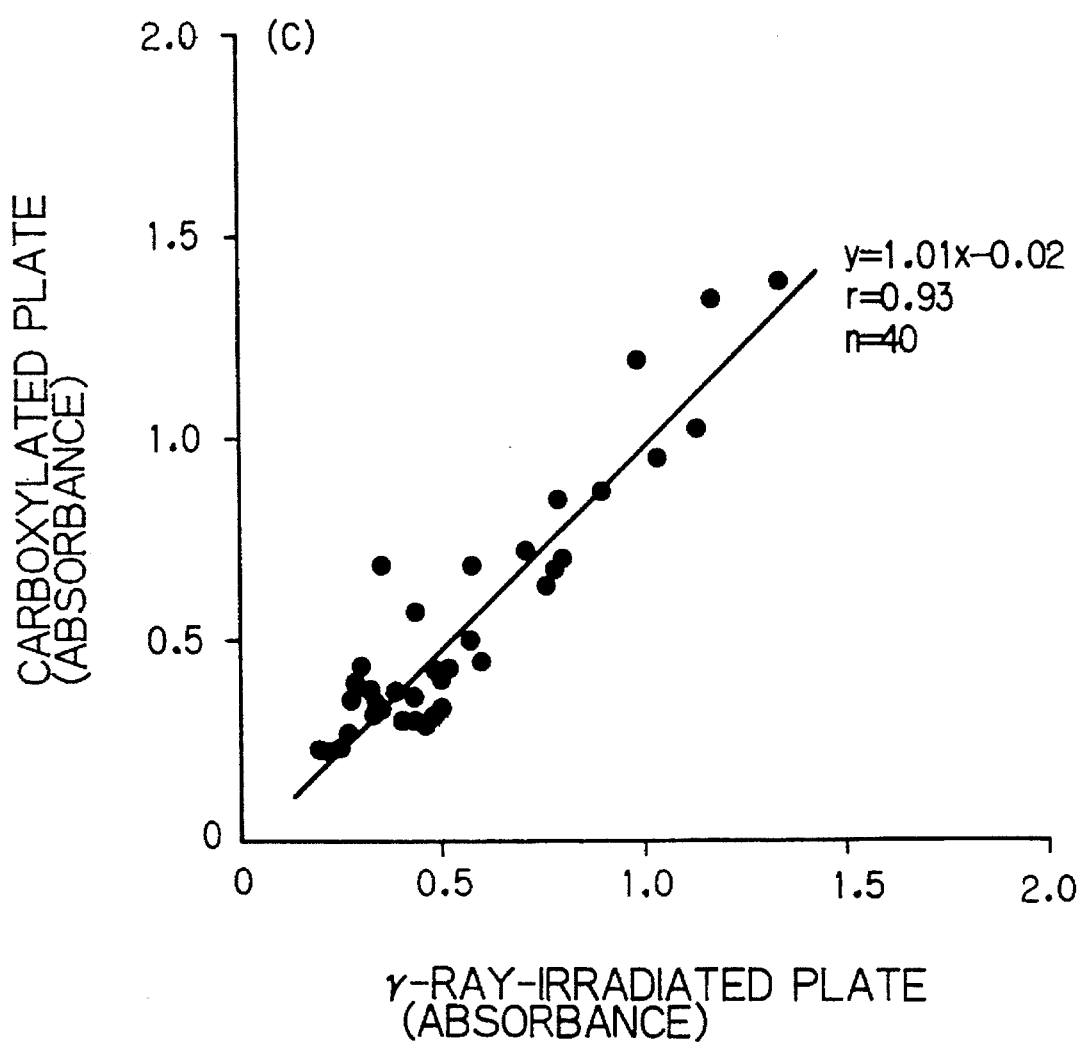
FIG. 12 shows the correlation between anticardiolipin antibody titers obtained using plates irradiated with radiation and those obtained using carboxylated plates.

(D): Correlation among anticardiolipin antibody titers obtained using plates irradiated with radiation, carboxylated plates and CL-coated plates Using plates exposed to γ ray of 100 kGray or carboxylated plates to which β2-GPI had been coated, antibody titers in the APS-derived serum collected from the anticardiolipin antibody positive patient were assayed in the same manner as in the above assay (A). In addition, the anticardiolipin antibody titer was assayed by the improved assay method by Matsuura et al. (WO91/06006). Correlation in measurement data (absorbance) among the three assay methods was thus examined. As shown in FIGS. 10 through 12, a high correlation was noted among the three assay methods.

Figure 13:
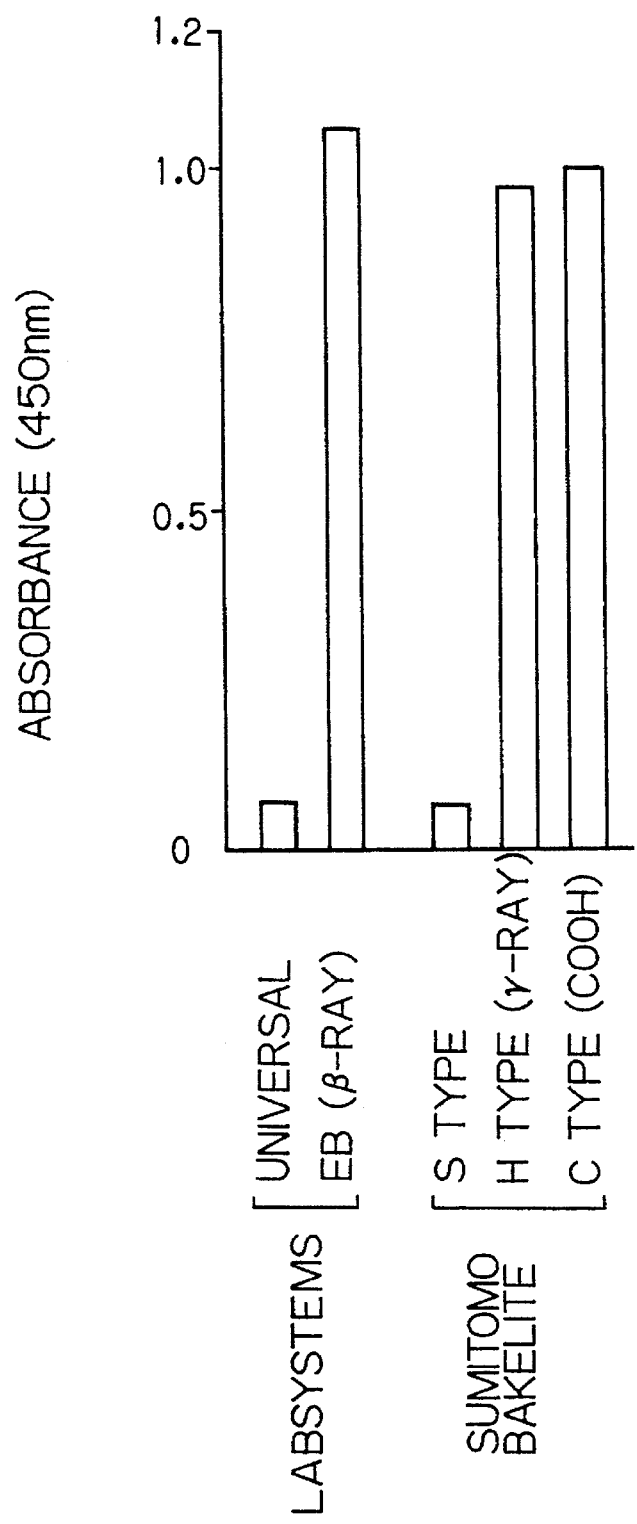
FIG. 13 shows the results of anticardiolipin determination using commercially available polystyrene plates on which β2-GPI has been previously coated.

(E): Assay for anticardiolipin antibodies using β2-GPI coated on commercially available polystyrene plates The basic procedures for this assay are the same as in the above assay (A). The plates used are Universal Plate (intact plate) and EB Plate by Labsystems Co., Ltd., and S type (intact plate), H type (y ray-exposed plate) and C type (carboxylated plate) by Sumitomo Bakelite Co., Ltd. As shown in FIG. 13, it became possible to assay for the anticardiolipin antibodies by using the plate obtained by exposure to β ray or γ ray, or by using the plate obtained by introduction of carboxyl groups through chemical modification.

Example 3: Differential assay for respective anticardiolipin antibodies specific to autoimmune and infectious diseases After 50 μl each of purified β2-GPI (10 μg/ml, prepared with Hepes) was added to each well of a carboxylated plate (C type, manufactured by Sumitomo Bakelite Co., Ltd.), incubation was performed at 4° C. overnight. In the control group, Hepes buffer described above was charged. After washing three times with PBS-TWEEN, gelatin-PBS (200 μl) was added to effect blocking at room temperature for an hour. After gelatin-PBS was removed, 100 μl each of serum sample diluted to 200 fold with Hepes-PBS was added to each well and then settled at room temperature for 30 minutes. Thereafter, the same procedures as in Example 2 (A) were conducted. As shown in FIG. 14, the APS-derived anticardiolipin antibodies showed binding only to the plate coated with β2-GPI, whereas the syphilis-derived antibodies were specifically bound to the carboxylated plates independently of β2-GPI.

Figure 15A:
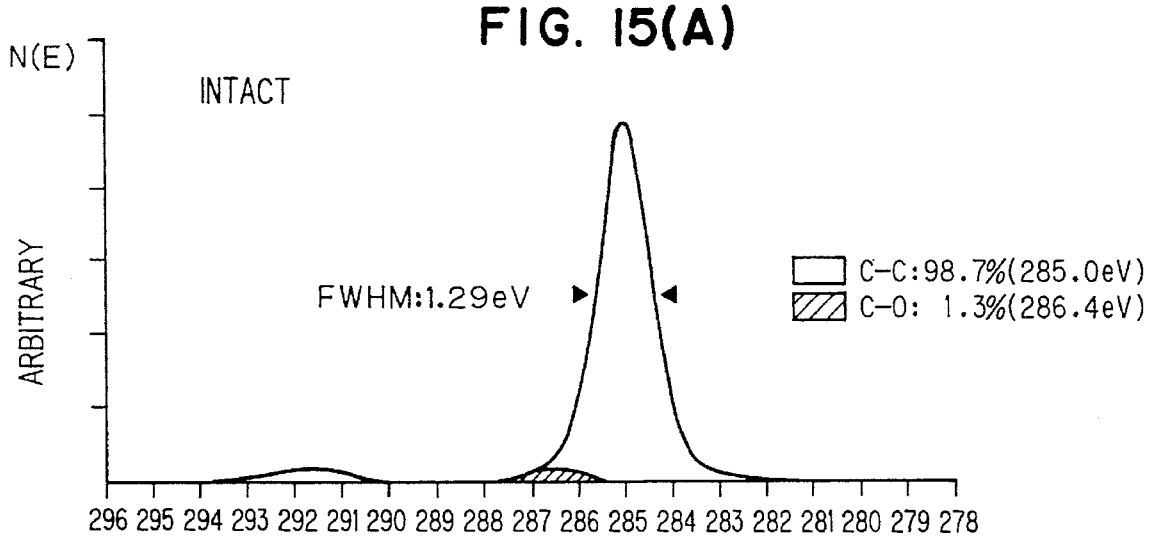
FIGS. 15(A)–15(C) show the results of surface analysis of polystyrene plates of the present invention which were previously irradiated with radiation or electron by X-ray photoelectron spectroscopy.
Figure 15B:
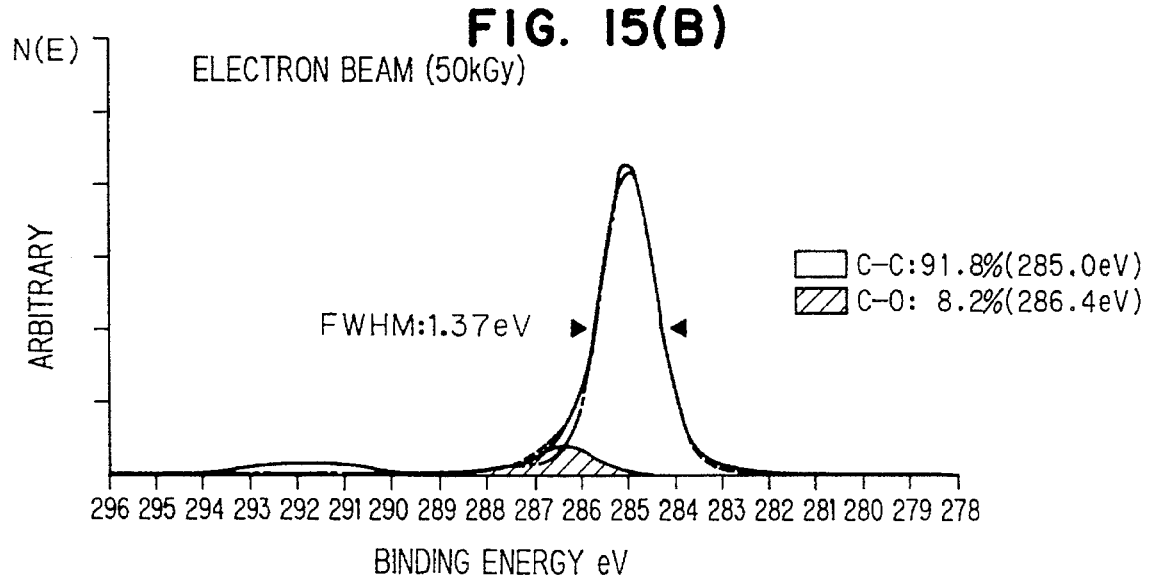
Figure 15C:
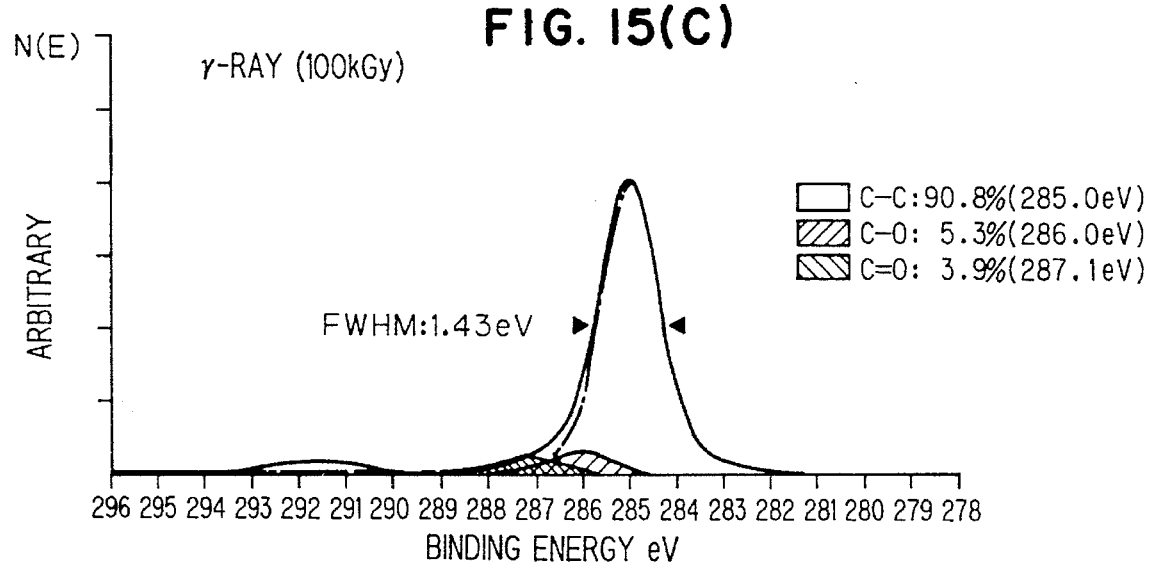

Example 4: Analysis of the surface of radiation-or electron beam-exposed polystyrene plate by x-ray photoelectron spectroscopy; XPS XPS analysis was performed by ESCA Spectrometer (JPS-9000MC, JEOL Ltd., Tokyo Japan). Survey scanning spectrum of 0–1000 ev and Cls spectrum were determined at MgKa 1,2 (1253.6 ev). In this case, the energy passed was 10 eV and resolution was 0.9 ev at the Ag 3d 5/2 peak. Correction was made by the C—C bond energy of the Cls peak as 285.0 ev. For the spectrum analysis, curve fitting of Gaussian/Lorentzian (80:20) was used. As shown in FIG. 15, C-0 (1.3%) was only slightly detected on the surface of intact plate as shown in panel (A). The plates exposed to electron beams (50 KGy) (panel (B)) and to γ ray (100 KGy) (panel (C)) showed C–0 (8.2%) and C–0 (5.3%), C=0 ( 3.9% ), indicating significant introduction of oxygen.

FIELD OF INDUSTRY APPLICABILITY

According to the present invention, antibodies specific to antiphospholipid syndrome can be specifically assayed by using only β2-glycoprotein I. The present invention does not, therefore, require a combination of β2-glycoprotein I and phospholipid for assaying antibodies specific to antiphospholipid syndrome, so that reagents for the assay can be prepared in an extremely simple manner.

Further, according to the present invention, antibodies specific to antiphospholipid syndrome can be assayed differentially from antibodies specific to infectious diseases, by using the solid phase reagent comprising a carrier having the surface on which functional groups containing a negative charge or a lone pair of electrons and/or free radicals having a negative charge or a lone pair of electrons have been previously introduced and having two sites on the surface, one of which has been coated with β2-glycoprotein and another which has been coated with no β2-glycoprotein; or by using two solid phase reagents, one of which comprises a carrier having a surface on which the function groups and/or free radicals have been introduced and having β2-glycoprotein coated on the surface, and another which comprises a carrier having the a surface on which the functional groups and/or free radicals have been introduced and having no β2-glycoprotein coated on the surface.

What is claimed are:

1. A solid phase reagent for detecting anticardiolipin antibodies which are specific to antiphospholipid syndrome, which reagent does not contain a phospholipid, said reagent consisting essentially of a synthetic resin having a protein-adsorbable hydrophobic surface which is derivatized with at least one group consisting of functional groups and free radicals, said functional groups and free radicals having a negative charge, a lone pair of electrons, or both, provided that said functional groups and free radicals are not phospholipids, and which resin further has β2-glycoprotein I bound to said derivatized surface.

2. The solid phase reagent according to claim 1, wherein said synthetic resin is derivatized by exposing the resin to radiation or electron beams.

3. The solid phase reagent according to claim 1, wherein said synthetic resin is derivatized by treating the resin with ozone or plasma.

4. The solid phase reagent according to claim 1, wherein said functional groups, free radicals, or both, contain an oxygen atom.

5. The solid phase reagent according to claim 1, wherein said functional groups are selected from the group consisting of hydroxy, carboxyl, carbonyl, formyl, imino, nitro, thiol and sulfonyl.

6. A method for detecting anticardiolipin antibodies which are specific to antiphospholipid syndrome, which method does not utilize a phospholipid, said method consisting essentially of the steps of:

contacting a fluid test sample with a solid phase reagent, said reagent consisting essentially of a synthetic resin having a protein-adsorbable hydrophobic surface which is derivatized with at least one group consisting of functional groups and free radicals, said functional groups and free radicals having a negative charge, a lone pair of electrons, or both, provided that said functional groups and free radicals are not phospholipids, and which resin further has β2-glycoprotein I bound to said derivatized surface, to specifically bind anticardiolipin antibodies in the fluid test sample which are specific to antiphospholipid syndrome to the β2-glycoprotein I of the solid phase reagent, and detecting the specifically bound anticardiolipin antibodies.

7. A kit for use in detecting anticardiolipin antibodies in a fluid test sample which are specific to antiphospholipid syndrome, which kit does not contain a phospholipid, said kit comprising:

a solid phase reagent consisting essentially of a synthetic resin having a protein-adsorbable hydrophobic surface which is derivatized with at least one group consisting of functional groups and free radicals, said functional groups and free radicals having a negative charge, a lone pair of electrons, or both, provided that said functional groups and free radicals are not phospholipids, and which resin further has β2-glycoprotein I bound to said derivatized surface, and means for detecting anticardiolipin antibodies bound to the solid phase reagent which are specific to antiphospholipid syndrome, which means do not contain a phospholipid.

8. The kit according to claim 7, wherein said means for detecting anticardiolipin antibodies bound to the solid phase reagent which are specific to antiphospholipid syndrome comprises a labelled anti-immunoglobulin antibody and a standard solution of anticardiolipin antibodies which are specific to antiphospholipid syndrome.

9. A solid phase reagent for detecting anticardiolipin antibodies which are specific to antiphospholipid syndrome, which reagent does not contain a phospholipid, said reagent consisting essentially of a synthetic resin having a protein-adsorbable hyrophobic surface which is derivatized with at least one group consisting of functional groups and free radicals, said functional groups and free radicals having a negative charge, a lone pair of electrons, or both, provided that said functional groups and free radicals are not phospholipids, said derivatized surface having a plurality of binding sites for β2-glycoprotein I and wherein β2-glycoprotein I is bound to only a portion of said plurality of binding sites on said derivatized surface.

10. A method for selectively detecting anticardiolipin antibodies which are specific to antiphospholipid syndrome differentially from anticardiolipin antibodies which are specific to infectious diseases, which method does not utilize a phospholipid, said method consisting essentially of the steps of:

contacting a fluid test sample with a solid phase reagent consisting essentially of a synthetic resin having a protein-adsorbable hydrophobic surface which is derivatized with at least one group consisting of functional groups and free radicals, said functional groups and free radicals having a negative charge, a lone pair of electrons, or both, provided that said functional groups and free radicals are not phospholipids, said derivatized surface having a plurality of binding sites for β2-glycoprotein I, and whereinβ2-glycoprotein I is bound to only a portion of said plurality of binding sites on said derivatized surface, wherein anticardiolipin antibodies in the fluid test sample which are specific to antiphospholipid syndrome are specifically bound to the β2-glycoprotein I of the solid phase reagent, whereas anticardiolipin antibodies in the fluid test sample which are specific to infectious diseases are bound to the solid phase reagent independently of β2-glycoprotein I.

and comparing the extent of binding by anticardiolipin antibodies in the fluid test sample to said derivatized surface having β2-glycoprotein I bound thereto with the extent of binding by anticardiolipin antibodies in the fluid test sample to said derivatized surface having no β2-glycoprotein I bound thereto, thereby to differentially determine anticardiolipin antibodies in the fluid test sample which are specific to antiphospholipid syndrome from anticardiolipin antibodies which are specific to infectious diseases.

11. A kit for use in differentially detecting anticardiolipin antibodies which are specific to antiphospholipid syndrome from anticardiolipin antibodies which are specific to infectious diseases, which kit does not contain a phospholipid, said kit comprising:

a solid phase reagent consisting essentially of a synthetic resin having a protein-adsorbable hydrophobic surface which is derivatized with at least one group consisting of functional groups and free radicals, said functional groups and free radicals having a negative charge, a lone pair of electrons, or both, provided that said functional groups and free radicals are not phospholipids, said derivatized surface having a plurality of binding sites for β2-glycoprotein I. and wherein β2-glycoprotein I is bound to only a portion of said plurality of binding sites on said derivatized surface, and means for differentially detecting anticardiolipin antibodies which are specific to antiphospholipid syndrome from anticardiolipin antibodies which are specific to infectious diseases, which means do not contain a phospholipid.

12. The kit according to claim 11, wherein said means to differentially detecting anticardiolipin antibodies which are specific to antiphospholipid syndrome from anticardiolipin antibodies which are specific to infectious diseases comprises a labelled anti-immunoglobulin antibody, a standard solution of anticardiolipin antibodies which are specific to antiphospholipid syndrome, and a standard solution of anticardiolipin antibodies which are specific to infectious diseases.

13. A method for selectively detecting anticardiolipin antibodies which are specific to antiphospholipid syndrome differentially from anticardiolipid antibodies which are specific to infectious diseases, which method does not utilize a phospholipid, said method consisting essentially of the steps of:

contacting a fluid test sample with first and second solid phase reagents, said first solid phase reagent consisting essentially of a synthetic resin having a protein-adsorbable hydrophobic surface which is derivatized with at least one group consisting of functional groups and free radicals, said functional groups and free radicals having a negative charge, a lone pair of electrons, or both, provided that said functional groups and free radicals are not phospholipids, and which resin further has β2-glycoprotein I bound to said derivatized surface, said second solid phase reagent being substantially identical to said first solid phase reagent except that it has no β2-glycoprotein I bound to said derivatized surface, wherein anticardiolipin antibodies in the fluid test sample which are specific to antiphospholipid syndrome are specifically bound to the β2-glycoprotein I of said first solid phase reagent, whereas anticardiolipin antibodies in the fluid test sample which are specific to infectious diseases are bound to said solid phase reagents independently of β2-glycoprotein I.

and comparing the extent of binding by anticardiolipin antibodies in the fluid test sample to said derivatized surface of said first solid phase reagent having β2-glycoprotein I bound thereto with the extent of binding by anticardiolipin antibodies in the fluid test sample to said derivatized surface of said second solid phase reagent having no β2-glycoprotein I bound thereto, thereby to differentially determine anticardiolipin antibodies in the fluid test sample which are specific to antiphospholipid syndrome from anticardiolipin antibodies which are specific to infectious diseases.

14. A kit for use in differentially detecting anticardiolipin antibodies specific to antiphospholipid syndrome from anticardiolipin antibodies specific to infectious diseases, which kit does not contain a phospholipid, said kit comprises:

a first solid phase reagent consisting essentially of a synthetic resin having a protein-adsorbable hydrophobic surface which is derivatized with at least one group consisting of functional groups and free radicals, said functional groups and free radicals having a negative charge, a lone pair of electrons, or both, provided that said functional groups and free radicals are not phospholipids, and which resin further has β2-glycoprotein I bound to said derivatized surface, a second solid phase reagent which is substantially identical to said first solid phase reagent except that it has no β2-glycoprotein I bound to said derivatized surface, and means for differentially detecting anticardiolipin antibodies which are specific to antiphospholipid syndrome from anticardiolipin antibodies which are specific to infectious diseases, which means do not contain a phospholipid.

15. The kit according to claim 14, wherein said means for differentially detecting anticardiolipin antibodies which are specific to antiphospholipid syndrome from anticardiolipin antibodies which are specific to infectious diseases comprises a labelled anti-immunoglobulin antibody, a standard solution of anticardiolipin antibodies which are specific to antiphospholipid syndrome, and a standard solution of anticardiolipin antibodies which are specific to infectious diseases.

\* \* \* \* \*